(12) United States Patent
Gerardi et al.

(10) Patent No.: US 12,274,779 B2
(45) Date of Patent: Apr. 15, 2025

(54) EFFERVESCENT ORAL COMPOSITION

(71) Applicant: NICOVENTURES TRADING LIMITED, London (GB)

(72) Inventors: Anthony Richard Gerardi, Winston-Salem, NC (US); Ross Jay Oden, Winston-Salem, NC (US); Matthew Evan Lampe, Winston-Salem, NC (US); Kristen Ann Spielbauer, Kernersville, NC (US); Nicolas von Cosmos, Moravian Falls, NC (US); Michael Andrew Zawadzki, Durham, NC (US)

(73) Assignee: NICOVENTURES TRADING LIMITED, London (GB)

( * ) Notice: Subject to any disclaimer, the term of this patent is extended or adjusted under 35 U.S.C. 154(b) by 675 days.

(21) Appl. No.: 17/340,621

(22) Filed: Jun. 7, 2021

(65) Prior Publication Data
US 2021/0378948 A1    Dec. 9, 2021

Related U.S. Application Data

(63) Continuation of application No. PCT/IB2021/054880, filed on Jun. 3, 2021.
(Continued)

(51) Int. Cl.
| | | |
|---|---|---|
| *A61K 9/46* | (2006.01) |
| *A23L 29/00* | (2016.01) |
| *A23L 29/30* | (2016.01) |
| *A23L 33/105* | (2016.01) |
| *A23L 33/125* | (2016.01) |
| *A23L 33/15* | (2016.01) |
| *A23L 33/16* | (2016.01) |
| *A23L 33/175* | (2016.01) |
| *A24B 13/00* | (2006.01) |
| *A24B 15/16* | (2020.01) |
| *A61K 9/00* | (2006.01) |
| *A61K 9/20* | (2006.01) |
| *A61K 31/198* | (2006.01) |
| *A61K 31/375* | (2006.01) |
| *A61K 31/522* | (2006.01) |
| *A61K 47/02* | (2006.01) |
| *A61K 47/12* | (2006.01) |
| *A61K 47/26* | (2006.01) |
| *A61K 47/36* | (2006.01) |

(52) U.S. Cl.
CPC .......... *A61K 9/0007* (2013.01); *A23L 29/015* (2016.08); *A23L 29/035* (2016.08); *A23L 29/045* (2016.08); *A23L 29/37* (2016.08); *A23L 33/105* (2016.08); *A23L 33/125* (2016.08); *A23L 33/15* (2016.08); *A23L 33/16* (2016.08); *A23L 33/175* (2016.08); *A24B 13/00* (2013.01); *A24B 15/16* (2013.01); *A61K 9/0053* (2013.01); *A61K 9/009* (2013.01); *A61K 9/2009* (2013.01); *A61K 9/2013* (2013.01); *A61K 9/2018* (2013.01); *A61K 31/198* (2013.01); *A61K 31/375* (2013.01); *A61K 31/522* (2013.01); *A61K 47/02* (2013.01); *A61K 47/12* (2013.01); *A61K 47/26* (2013.01); *A61K 47/36* (2013.01); *A23V 2002/00* (2013.01)

(58) Field of Classification Search
CPC .............. A61K 31/198; A61K 2300/00; A61K 31/197; A61K 31/522; A61K 31/185; A61K 31/375; A61K 36/258; A61K 36/752; A61K 9/0007; A61K 9/0053; A61K 9/009; A61K 9/2009; A61K 9/2013; A61K 9/2018; A61K 47/02; A61K 47/12; A61K 47/26; A61K 47/36; A61K 9/0056; A61K 9/006; A61K 9/0095; A61K 9/145; A61K 9/1623; A61K 9/2059; A61K 9/2095; A61K 31/465; A61K 47/10; A61K 47/38; A23L 29/015; A23L 29/035; A23L 29/045; A23L 29/37; A23L 33/105; A23L 33/125; A23L 33/15; A23L 33/16; A23L 33/175; A24B 13/00; A24B 15/16; A24B 15/281; A23V 2002/00; A23P 10/40
See application file for complete search history.

(56) References Cited

U.S. PATENT DOCUMENTS

| | | |
|---|---|---|
| 2,033,909 A | 3/1936 | Cox et al. |
| 4,289,794 A | 9/1981 | Kleiner et al. |

(Continued)

FOREIGN PATENT DOCUMENTS

| | | |
|---|---|---|
| CN | 103005680 | 4/2013 |
| CN | 103263507 | 8/2013 |

(Continued)

OTHER PUBLICATIONS

Wei et al. (WO2020078036A1 Machine Translation) (Year: 2020).*
(Continued)

*Primary Examiner* — Robert A Wax
*Assistant Examiner* — Quanglong N Truong
(74) *Attorney, Agent, or Firm* — WOMBLE BOND DICKINSON (US) LLP; Scott Breining

(57) ABSTRACT

The disclosure provides an effervescent composition adapted for oral use, the composition including an effervescent material; one or more fillers in a total amount of at least about 30% by weight, the one or more fillers including at least one sugar alcohol; at least one active ingredient; and optionally, a lipid in an amount of at least about 20% by weight. Melting effervescent compositions are also provided, which include the lipid.

38 Claims, 3 Drawing Sheets

Related U.S. Application Data

(60) Provisional application No. 63/036,251, filed on Jun. 8, 2020.

(56) References Cited

U.S. PATENT DOCUMENTS

| | | | |
|---|---|---|---|
| 4,639,368 A | 1/1987 | Niazi et al. | |
| 4,725,427 A | 2/1988 | Ashmead et al. | |
| 5,165,951 A | 11/1992 | Gallart et al. | |
| 5,178,878 A | 1/1993 | Wehling et al. | |
| 5,223,264 A | 6/1993 | Wehling et al. | |
| 5,417,229 A | 5/1995 | Summers et al. | |
| 5,439,698 A | 8/1995 | Ahn et al. | |
| 5,762,951 A * | 6/1998 | Maasz | A61K 9/0007 514/159 |
| 6,138,683 A | 10/2000 | Hersh et al. | |
| 6,845,777 B2 | 1/2005 | Pera | |
| 6,887,307 B1 | 5/2005 | Scott et al. | |
| 6,923,981 B2 | 8/2005 | Leung et al. | |
| 6,958,143 B2 | 10/2005 | Choi et al. | |
| 6,974,590 B2 | 12/2005 | Pather et al. | |
| 7,032,601 B2 | 4/2006 | Atchley et al. | |
| 7,056,541 B1 | 6/2006 | Stahl et al. | |
| 7,381,667 B2 | 6/2008 | Bergquist et al. | |
| 7,507,427 B2 | 3/2009 | Andersen et al. | |
| 7,810,507 B2 | 10/2010 | Dube et al. | |
| 7,833,555 B2 | 11/2010 | Andersen et al. | |
| 7,861,728 B2 | 1/2011 | Holton, Jr. et al. | |
| 7,900,637 B2 | 3/2011 | Fagerstrom et al. | |
| 7,950,399 B2 | 5/2011 | Winterson et al. | |
| 8,069,861 B2 | 12/2011 | Sinclair | |
| 8,124,147 B2 | 2/2012 | Cheng et al. | |
| 8,293,295 B2 | 10/2012 | Andersen et al. | |
| 8,336,557 B2 | 12/2012 | Kumar et al. | |
| 8,343,532 B2 | 1/2013 | Dam et al. | |
| 8,424,541 B2 | 4/2013 | Crawford et al. | |
| 8,469,036 B2 | 6/2013 | Williams et al. | |
| 8,469,037 B2 | 6/2013 | Liu et al. | |
| 8,529,875 B2 | 9/2013 | Andersen | |
| 8,529,914 B2 | 9/2013 | Fuisz et al. | |
| 8,545,870 B2 | 10/2013 | Dupinay et al. | |
| 8,591,967 B2 | 11/2013 | Andersen et al. | |
| 8,613,285 B2 | 12/2013 | Fuisz | |
| 8,627,828 B2 | 1/2014 | Strickland et al. | |
| 8,642,016 B2 | 2/2014 | Chau et al. | |
| 8,714,163 B2 | 5/2014 | Kumar et al. | |
| 8,741,348 B2 | 6/2014 | Hansson et al. | |
| 8,747,562 B2 | 6/2014 | Mishra et al. | |
| 8,828,361 B2 | 9/2014 | Anderson | |
| 8,833,378 B2 | 9/2014 | Axelsson et al. | |
| 8,846,075 B2 | 9/2014 | Johnson et al. | |
| 8,858,984 B2 | 10/2014 | Dam et al. | |
| 8,863,755 B2 | 10/2014 | Zhuang et al. | |
| 8,871,243 B2 | 10/2014 | Fankhauser et al. | |
| 8,931,493 B2 | 1/2015 | Sebastian et al. | |
| 8,945,593 B2 | 2/2015 | LoCoco et al. | |
| 8,978,661 B2 | 3/2015 | Atchley et al. | |
| 8,992,974 B2 | 3/2015 | McCarty | |
| 9,027,567 B2 | 5/2015 | Gee et al. | |
| 9,039,839 B2 | 5/2015 | Beeson et al. | |
| 9,044,035 B2 | 6/2015 | Jackson et al. | |
| 9,084,439 B2 | 7/2015 | Holton, Jr. | |
| 9,155,321 B2 | 10/2015 | Cantrell et al. | |
| 9,161,567 B2 | 10/2015 | Shikata et al. | |
| 9,161,908 B2 | 10/2015 | Nilsson | |
| 9,167,835 B2 | 10/2015 | Sengupta et al. | |
| 9,185,931 B2 | 11/2015 | Gao et al. | |
| 9,204,667 B2 | 12/2015 | Cantrell et al. | |
| 9,237,768 B2 | 1/2016 | Carroll et al. | |
| 9,237,769 B2 | 1/2016 | Mua et al. | |
| 9,358,296 B2 | 6/2016 | McCarty | |
| 9,372,033 B2 | 6/2016 | Lampe et al. | |
| 9,386,800 B2 | 7/2016 | Sebastian et al. | |
| 9,402,414 B2 | 8/2016 | Griscik et al. | |
| 9,402,809 B2 | 8/2016 | Axelsson et al. | |
| 9,414,624 B2 | 8/2016 | Carroll et al. | |
| 9,420,825 B2 | 8/2016 | Beeson et al. | |
| 9,468,233 B2 | 10/2016 | Macko et al. | |
| 9,474,303 B2 | 10/2016 | Holton, Jr. | |
| 9,521,864 B2 | 12/2016 | Gao et al. | |
| 9,565,867 B2 | 2/2017 | Wittorff et al. | |
| 9,629,392 B2 | 4/2017 | Holton, Jr. | |
| 9,635,881 B2 | 5/2017 | Sjögren et al. | |
| 9,675,102 B2 | 6/2017 | Hunt et al. | |
| 9,763,928 B2 | 9/2017 | Duggins et al. | |
| 9,775,376 B2 | 10/2017 | Cantrell et al. | |
| 9,801,409 B1 | 10/2017 | Smith | |
| 9,848,634 B2 | 12/2017 | Fuisz | |
| 9,854,830 B2 | 1/2018 | Gao et al. | |
| 9,884,015 B2 | 2/2018 | Gao et al. | |
| 9,907,748 B2 | 3/2018 | Borschke et al. | |
| 9,925,145 B2 | 3/2018 | Hubinette et al. | |
| 9,930,909 B2 | 4/2018 | Gao et al. | |
| 9,999,243 B2 | 6/2018 | Gao et al. | |
| 10,039,309 B2 | 8/2018 | Carroll et al. | |
| 10,045,976 B2 | 8/2018 | Fusco et al. | |
| 10,092,715 B2 | 10/2018 | Axelsson et al. | |
| 10,130,120 B2 | 11/2018 | Mishra et al. | |
| 10,143,230 B2 | 12/2018 | Mishra et al. | |
| 10,149,850 B2 | 12/2018 | Mishra et al. | |
| 10,172,810 B2 | 1/2019 | McCarty | |
| 10,244,786 B2 | 4/2019 | Gao et al. | |
| 10,334,873 B2 | 7/2019 | Mishra et al. | |
| 10,357,054 B2 | 7/2019 | Marshall et al. | |
| 10,375,984 B2 | 8/2019 | Hernandez Garcia et al. | |
| 10,390,557 B2 | 8/2019 | Börjesson et al. | |
| 10,426,726 B2 | 10/2019 | Neergaard | |
| 10,463,070 B2 | 11/2019 | Carroll et al. | |
| 10,532,046 B2 | 1/2020 | Rogers et al. | |
| 10,543,205 B2 | 1/2020 | Wittorff et al. | |
| 2004/0118422 A1 | 6/2004 | Lundin et al. | |
| 2006/0019154 A1 | 1/2006 | Strickland et al. | |
| 2007/0031539 A1 | 2/2007 | Calton | |
| 2007/0062549 A1 | 3/2007 | Holton, Jr. et al. | |
| 2008/0081071 A1 | 4/2008 | Sanghvi et al. | |
| 2008/0166395 A1 | 7/2008 | Roush | |
| 2009/0023819 A1 | 1/2009 | Axelsson | |
| 2009/0025741 A1 | 1/2009 | Crawford et al. | |
| 2009/0065013 A1 | 3/2009 | Essen et al. | |
| 2009/0253754 A1 | 10/2009 | Selmin et al. | |
| 2009/0301504 A1 | 12/2009 | Worthen et al. | |
| 2010/0004294 A1 | 1/2010 | Axelsson et al. | |
| 2010/0018539 A1 | 1/2010 | Brinkley et al. | |
| 2010/0061940 A1 | 3/2010 | Axelsson et al. | |
| 2010/0170522 A1 | 7/2010 | Sun et al. | |
| 2010/0187143 A1 | 7/2010 | Essen et al. | |
| 2010/0247586 A1 * | 9/2010 | Hugerth | A61K 31/465 424/440 |
| 2010/0260690 A1 | 10/2010 | Kristensen et al. | |
| 2010/0291245 A1 | 11/2010 | Gao et al. | |
| 2010/0294292 A1 | 11/2010 | Hodin et al. | |
| 2011/0014132 A1 | 1/2011 | Shuang | |
| 2011/0139164 A1 | 6/2011 | Mua et al. | |
| 2011/0220130 A1 | 9/2011 | Mua et al. | |
| 2011/0268809 A1 | 11/2011 | Brinkley et al. | |
| 2012/0031415 A1 | 2/2012 | Essen et al. | |
| 2012/0037175 A1 | 2/2012 | Cantrell et al. | |
| 2012/0055494 A1 | 3/2012 | Hunt et al. | |
| 2013/0078307 A1 | 3/2013 | Holton, Jr. et al. | |
| 2013/0118512 A1 | 5/2013 | Jackson et al. | |
| 2013/0152953 A1 | 6/2013 | Mua et al. | |
| 2013/0177646 A1 | 7/2013 | Hugerth et al. | |
| 2013/0206150 A1 | 8/2013 | Duggins et al. | |
| 2013/0251779 A1 | 9/2013 | Svandal et al. | |
| 2013/0340773 A1 | 12/2013 | Sebastian et al. | |
| 2014/0130813 A1 | 5/2014 | Strehle | |
| 2014/0154301 A1 | 6/2014 | Chau et al. | |
| 2014/0255452 A1 | 9/2014 | Reddick et al. | |
| 2015/0068544 A1 | 3/2015 | Moldoveanu et al. | |
| 2015/0068545 A1 | 3/2015 | Moldoveanu et al. | |
| 2015/0071972 A1 | 3/2015 | Holton, Jr. et al. | |
| 2015/0096573 A1 | 4/2015 | Gao et al. | |
| 2015/0096574 A1 | 4/2015 | Gao et al. | |
| 2015/0096576 A1 | 4/2015 | Gao et al. | |

(56) References Cited

U.S. PATENT DOCUMENTS

| | | |
|---|---|---|
| 2015/0296868 A1 | 10/2015 | Sutton |
| 2016/0000140 A1 | 1/2016 | Sebastian et al. |
| 2016/0073676 A1 | 3/2016 | Cantrell et al. |
| 2016/0073689 A1 | 3/2016 | Sebastian et al. |
| 2016/0157515 A1 | 6/2016 | Chapman et al. |
| 2016/0192703 A1 | 7/2016 | Sebastian et al. |
| 2017/0007594 A1 | 1/2017 | Borschke |
| 2017/0071247 A1 | 3/2017 | Hunt et al. |
| 2017/0164651 A1 | 6/2017 | Mua et al. |
| 2017/0165252 A1 | 6/2017 | Mua et al. |
| 2017/0172995 A1 | 6/2017 | Repaka et al. |
| 2017/0280764 A1 | 10/2017 | Sahlen et al. |
| 2017/0312261 A1 | 11/2017 | Changoer et al. |
| 2017/0318858 A1 | 11/2017 | Hodin et al. |
| 2018/0140007 A1 | 5/2018 | Aspgren et al. |
| 2018/0140521 A1 | 5/2018 | Geonnotti et al. |
| 2018/0140554 A1 | 5/2018 | Wittorff |
| 2018/0153211 A1 | 6/2018 | Persson |
| 2018/0235273 A1 | 8/2018 | Carroll et al. |
| 2018/0255826 A1 | 9/2018 | Persson et al. |
| 2018/0257801 A1 | 9/2018 | Persson |
| 2019/0037909 A1 | 2/2019 | Greenbaum et al. |
| 2019/0174812 A1 | 6/2019 | Nielsen et al. |
| 2019/0175581 A1 | 6/2019 | Nielsen et al. |
| 2019/0255035 A1 | 8/2019 | Bruun |
| 2020/0037638 A1 | 2/2020 | Faraci et al. |
| 2020/0128870 A1 | 4/2020 | Hassler et al. |
| 2020/0138706 A1 | 5/2020 | Rudraraju et al. |
| 2020/0275689 A1 | 9/2020 | Lewerenz |
| 2020/0297026 A1 | 9/2020 | Kannisto et al. |
| 2020/0305496 A1 | 10/2020 | Gessesse |
| 2020/0383372 A1 | 12/2020 | Stahl et al. |
| 2020/0383373 A1 | 12/2020 | Stahl et al. |
| 2021/0378948 A1 | 12/2021 | Gerardi et al. |

FOREIGN PATENT DOCUMENTS

| | | | |
|---|---|---|---|
| CN | 103494324 | 1/2014 | |
| CN | 105192876 | 12/2015 | |
| CN | 105595404 | 5/2016 | |
| CN | 106107404 | 11/2016 | |
| CN | 110720529 | 1/2020 | |
| RU | 2221554 C2 | 1/2004 | |
| RU | 2675834 C2 | 12/2018 | |
| WO | 2007046890 A1 | 4/2007 | |
| WO | WO-2011113965 A1 * | 9/2011 | ........... A61K 31/352 |
| WO | WO2019/036243 | 2/2019 | |
| WO | WO 2020/078036 | 4/2020 | |
| WO | 2021250516 A1 | 12/2021 | |

OTHER PUBLICATIONS

JP2000072666A Machine Translation (Year: 2000).*
Robichaud Meagan et al., "Tobacco companies introduce 'tobacco free' nicotine pouches", Tob Control 2019, Nov. 21, 2019, 1-2, National Library of Medicine, doi:10.1136/tobaccocontrol-2019-055321.
"Opinion of the Scientific Panel on Food Additives, Flavourings, Processing Aids and Materials in Contact with Food on a request from the Commission related to Pullulan PI-20 for use as a new food additive" The EFSA Journal (2004) 85, 1-32.

* cited by examiner

EFFERVESCENT ORAL COMPOSITION

CROSS-REFERENCE TO RELATED APPLICATIONS

This application is a continuation of International Application No. PCT/IB2021/054880, filed on Jun. 3, 2021, and claims priority to U.S. Provisional Application No. 63/036,251, filed on Jun. 8, 2020, which are incorporated herein by reference in their entirety and for all purposes.

FIELD OF THE DISCLOSURE

The present disclosure relates to effervescent compositions intended for human use. The compositions are adapted for oral use and deliver substances such as flavors and/or active ingredients during use. Such compositions may include tobacco or a product derived from tobacco, or may be tobacco-free alternatives.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known. See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

Smokeless tobacco product configurations that combine tobacco material with various binders and fillers have been proposed more recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference.

BRIEF SUMMARY

The present disclosure generally provides effervescent compositions configured for oral use. The effervescent compositions comprise an effervescent material, one or more fillers, and a flavoring agent, an active ingredient, or both. Optionally, the effervescent compositions comprise a lipid. Surprisingly, it has been found according to the present disclosure that the presence of an effervescent effect in the oral cavity reduces the perception of bitterness associated with certain active ingredients which may be present in a composition adapted for oral use. Accordingly, in one aspect, the disclosure provides an effervescent composition adapted for oral use, comprising an effervescent material capable of causing effervescence in the oral cavity; one or more fillers in a total amount of at least about 30% by weight, based on the total weight of the effervescent composition, wherein the one or more fillers includes at least one sugar alcohol; at least one active ingredient; and optionally, a lipid in an amount of at least about 20% by weight.

In one embodiment, the effervescent material comprises an acid component and a base component, wherein the base component is a carbonate material, a bicarbonate material, or a mixture thereof.

In one embodiment, the acid component is a tricarboxylic acid, a dicarboxylic acid, or a combination thereof. In one embodiment, the acid component comprises a combination of a tricarboxylic acid and a dicarboxylic acid in a weight ratio of from about 2:1 to about 1:2. In one embodiment, the acid component is citric acid, tartaric acid, or a combination thereof. In one embodiment, the acid component is a combination of citric acid and tartaric acid in a ratio of from about 2:1 to about 1:2 by weight. In one embodiment, the acid component is a combination of citric acid and tartaric acid in a ratio of about 1:1 by weight.

In one embodiment, the base component is a bicarbonate material.

In one embodiment, the acid component is present in an amount of from about 10% to about 20% by weight, based on the total dry weight of the effervescent composition.

In one embodiment, the acid component and the base component are present in about a 1:1 molar ratio.

In one embodiment, the effervescent material has a particle size of less than about 180 microns.

In one embodiment, the effervescent material comprises a sugar material containing an entrapped gaseous component, such that release of the entrapped gaseous component occurs upon dissolution of the sugar material in the oral cavity. In one embodiment, the sugar material containing an entrapped gaseous component is in the form of a gasified sugar material in particulate form, the gasified sugar material particles being in admixture with the one or more fillers and active ingredient.

In one embodiment, the at least one active ingredient comprises one or more botanical materials, stimulants, amino acids, vitamins, cannabinoids, nutraceuticals, pharmaceutical agents, or combinations thereof. In one embodiment, the active ingredient comprises caffeine.

In one embodiments, the effervescent composition comprises from about 10 to about 25 dry weight percent of the effervescent material; at least about 50 dry weight percent of the one or more fillers; and from about 1 to about 10 dry weight percent of caffeine. In one embodiment, the one or more fillers comprises mannitol, maltodextrin, isomalt, polysaccharides, or a combination thereof.

In one embodiment, the one or more fillers comprises isomalt, glucose, and starch-derived polysaccharides. In one embodiment, a particle size of the filler is less than about 35 microns.

In one embodiment, the effervescent composition further comprises one or more additives selected from the group consisting of sweeteners, taste modifiers, salts, binders, buffering agents, colorants, humectants, oral care additives, preservatives, disintegration aids, antioxidants, flow aids, compressibility aids, and combinations thereof. In one embodiment, the particle size of any flavorants, sweeteners, taste modifiers, salts, binders, buffering agents, colorants, humectants, emulsifiers, oral care additives, preservatives, disintegration aids, antioxidants, flow aids, and compressibility aids which may be present is less than about 35 microns.

In one embodiment, the effervescent composition is substantially free of tobacco.

In one embodiment, the effervescent composition is substantially free of nicotine. In other embodiments, the active ingredient comprises a nicotine component.

In one embodiment, the effervescent composition is in granular form, wherein the effervescent composition in granular form is enclosed in a pouch to form a pouched product. In one embodiment, the pouch comprises a fleece material, wherein the fleece material has at least a portion of the acid component, the base component, or both, disposed thereon or impregnated therein.

In another embodiment, the effervescent composition is a compressed or extruded product having a predetermined shape. In one embodiment, the product is a tablet. In one embodiment, the product is a tablet having an aspect ratio (a ratio of diameter to height) of from about 1.5 to about 3.

In one embodiment, the lipid has a melting point of about 29° C. or above. In one embodiment, the lipid has a melting point from about 36° C. to about 45° C. In one embodiment, the lipid is an oil selected from the group consisting of palm oil, palm kernel oil, soybean oil, cottonseed oil, and combinations thereof, wherein the oil may be hydrogenated, partially hydrogenated, or non-hydrogenated.

In one embodiment, the effervescent composition comprises up to about 50 dry weight percent of the lipid; up to about 20 dry weight percent of the effervescent material; up to about 50 dry weight percent of the one or more fillers; and from about 1 to about 10 dry weight percent of caffeine.

In one embodiment, the effervescent composition comprises isomalt in an amount of from about 22 to about 33% by weight, based on the total weight of the effervescent composition; a glucose- and starch-derived polysaccharide blend in an amount of from about 30 to about 45% by weight, based on the total weight of the effervescent composition; a sweetener in an amount of from about 0.1 to about 0.5% by weight, based on the total weight of the effervescent composition; L-theanine in an amount of from about 3 to about 5% by weight, based on the total weight of the effervescent composition; gamma aminobutyric acid in an amount of from about 4 to about 6% by weight, based on the total weight of the effervescent composition; lemon balm extract in an amount of from about 2 to about 8% by weight, based on the total weight of the effervescent composition; tartaric acid in an amount of from about 4 to about 6% by weight, based on the total weight of the effervescent composition; citric acid in an amount of from about 4 to about 6% by weight, based on the total weight of the effervescent composition; sodium bicarbonate in an amount of from about 8 to about 15% by weight, based on the total weight of the effervescent composition; a salt in an amount of from about 0.1 to about 0.5% by weight, based on the total weight of the effervescent composition; and optionally, a processing aid.

In one embodiment, the effervescent composition comprises isomalt in an amount of from about 20 to about 30% by weight, based on the total weight of the effervescent composition; a glucose- and starch-derived polysaccharide blend in an amount of from about 30 to about 45% by weight, based on the total weight of the effervescent composition; a sweetener in an amount of from about 0.1 to about 0.5% by weight, based on the total weight of the effervescent composition; caffeine in an amount of from about 3 to about 5% by weight, based on the total weight of the effervescent composition; taurine in an amount of from about 4 to about 6% by weight, based on the total weight of the effervescent composition; vitamin C in an amount of from about 4 to about 6% by weight, based on the total weight of the effervescent composition; tartaric acid in an amount of from about 4 to about 6% by weight, based on the total weight of the effervescent composition; citric acid in an amount of from about 4 to about 6% by weight, based on the total weight of the effervescent composition; sodium bicarbonate in an amount of from about 8 to about 15% by weight, based on the total weight of the effervescent composition; a salt in an amount of from about 0.1 to about 0.5% by weight, based on the total weight of the effervescent composition; and optionally, a processing aid.

In one embodiment, the effervescent composition comprises isomalt in an amount of from about 22 to about 35% by weight, based on the total weight of the effervescent composition; a glucose and starch-derived polysaccharide blend in an amount of from about 28 to about 43% by weight, based on the total weight of the effervescent composition; a sweetener in an amount of from about 0.1 to about 0.5% by weight, based on the total weight of the effervescent composition; caffeine in an amount of from about 3 to about 5% by weight, based on the total weight of the effervescent composition; L-theanine in an amount of from about 4 to about 6% by weight, based on the total weight of the effervescent composition; citicoline or sunflower lecithin in an amount of from about 0.5 to about 1.5% by weight, based on the total weight of the effervescent composition; sodium citrate in an amount of from about 0.5 to about 1.5% by weight, based on the total weight of the effervescent composition; tartaric acid in an amount of from about 4 to about 6% by weight, based on the total weight of the effervescent composition; citric acid in an amount of from about 4 to about 6% by weight, based on the total weight of the effervescent composition; sodium bicarbonate in an amount of from about 8 to about 15% by weight, based on the total weight of the effervescent composition; a salt in an amount of from about 0.1 to about 0.5% by weight, based on the total weight of the effervescent composition; and optionally, a processing aid.

In one embodiment, the effervescent composition is in granular form, wherein the effervescent composition is enclosed in a pouch to form a pouched product. In one embodiment, the pouch comprises a fleece material, and wherein the fleece material has at least a portion of the acid component, the base component, or both disposed thereon or impregnated therein.

In another embodiment, the effervescent composition is in the form of a tablet. In one embodiment, the tablet has an outer surface, and the effervescent material is disposed on said outer surface. In one embodiment, the tablet comprises an inner region comprising the lipid. In one embodiment, the tablet comprises multiple layers comprising: an effervescent layer comprising the effervescent material; and at least one non-effervescent layer.

The disclosure includes, without limitations, the following embodiments.

Embodiment 1: An effervescent composition adapted for oral use, comprising: an effervescent material capable of causing effervescence in the oral cavity; one or more fillers in a total amount of at least about 30% by weight, based on the total weight of the composition, wherein the one or more fillers includes at least one sugar alcohol; optionally, a lipid in an amount of at least about 20% by weight; and a flavoring agent, an active ingredient, or both.

Embodiment 2: The effervescent composition of embodiment 1, wherein the effervescent material comprises an acid component and a base component, wherein the base component is a carbonate material, a bicarbonate material, or a mixture thereof.

Embodiment 3: The effervescent composition of embodiment 1 or 2, wherein the acid component is a tricarboxylic acid, a dicarboxylic acid, or a combination thereof.

Embodiment 4: The effervescent composition of any one of embodiments 1-3, wherein the acid component comprises a combination of a tricarboxylic acid and a dicarboxylic acid in a weight ratio of from about 2:1 to about 1:2.

Embodiment 5: The effervescent composition of any one of embodiments 1-4, wherein the acid component is citric acid, tartaric acid, or a combination thereof.

Embodiment 6: The effervescent composition of any one of embodiments 1-5, wherein the acid component is a combination of citric acid and tartaric acid in a ratio of from about 2:1 to about 1:2 by weight.

Embodiment 7: The effervescent composition of any one of embodiments 1-6, wherein the wherein the base component is a bicarbonate material.

Embodiment 8: The effervescent composition of any one of embodiments 1-7, wherein the acid component is present in an amount of from about 10% to about 20% by weight, based on the total dry weight of the effervescent composition.

Embodiment 9: The effervescent composition of any one of embodiments 1-8, wherein the acid component and the base component are present in about a 1:1 molar ratio.

Embodiment 10: The effervescent composition of any one of embodiments 1-9, wherein the effervescent material has a particle size of less than about 180 microns.

Embodiment 11: The effervescent composition of any one of embodiments 1-10, wherein the effervescent material comprises a sugar material containing an entrapped gaseous component, such that release of the entrapped gaseous component occurs upon dissolution of the sugar material in the oral cavity.

Embodiment 12: The effervescent composition of any one of embodiments 1-11, wherein the sugar material containing an entrapped gaseous component is in the form of a gasified sugar material in particulate form, the gasified sugar material particles being in admixture with the one or more fillers and active ingredient.

Embodiment 13: The effervescent composition of any one of embodiments 1-12, wherein the active ingredient comprises one or more botanical materials, stimulants, amino acids, vitamins, cannabinoids, cannabimimetics, terpenes, nutraceuticals, pharmaceutical agents, or a combination thereof.

Embodiment 14: The effervescent composition of any one of embodiments 1-13, wherein the active ingredient comprises caffeine.

Embodiment 15: The composition of any one of embodiments 1-14, comprising: from about 10 to about 25 dry weight percent of the effervescent material; at least about 50 dry weight percent of the one or more fillers; and from about 1 to about 10 dry weight percent of caffeine.

Embodiment 16: The effervescent composition of any one of embodiments 1-15, wherein the one or more fillers comprises mannitol, maltodextrin, isomalt, polysaccharides, and combinations thereof.

Embodiment 17: The effervescent composition of any one of embodiments 1-16, wherein the one or more fillers comprises isomalt, glucose, and starch-derived polysaccharides.

Embodiment 18: The effervescent composition of any one of embodiments 1-17, wherein a particle size of the filler is less than about 35 microns.

Embodiment 19: The effervescent composition of any one of embodiments 1-18, further comprising one or more additives selected from the group consisting of sweeteners, taste modifiers, salts, binders, buffering agents, colorants, humectants, oral care additives, preservatives, disintegration aids, antioxidants, flow aids, compressibility aids, and combinations thereof.

Embodiment 20: The effervescent composition of any one of embodiments 1-19, wherein a particle size of any flavorants, sweeteners, taste modifiers, salts, binders, buffering agents, colorants, humectants, emulsifiers, oral care additives, preservatives, disintegration aids, antioxidants, flow aids, and compressibility aids which may be present is less than about 35 microns.

Embodiment 21: The effervescent composition of any one of embodiments 1-20, wherein the effervescent composition is substantially free of tobacco.

Embodiment 22: The effervescent composition of any one of embodiments 1-21, wherein the effervescent composition is substantially free of nicotine.

Embodiment 23: The effervescent composition of any one of embodiments 1-22, wherein the active ingredient comprises a nicotine component.

Embodiment 24: The effervescent composition of any one of embodiments 1-23, wherein the effervescent composition is a compressed or extruded product having a predetermined shape.

Embodiment 25: The effervescent composition of any one of embodiments 1-24, wherein the compressed or extruded product is a tablet.

Embodiment 26: The effervescent composition of any one of embodiments 1-25, wherein the compressed or extruded product is a tablet having an aspect ratio of from about 1.5 to about 3.

Embodiment 27: The effervescent composition of any one of embodiments 1-24, wherein the effervescent composition is in granular form, and wherein the effervescent composition in granular form is enclosed in a pouch to form a pouched product.

Embodiment 28: The effervescent composition of any one of embodiments 1-27, wherein the lipid has a melting point of about 29° C. or above.

Embodiment 29: The effervescent composition of any one of embodiments 1-28, wherein the lipid has a melting point from about 36° C. to about 45° C.

Embodiment 30: The effervescent composition of any one of embodiments 1-29, wherein the lipid is an oil selected from the group consisting of palm oil, palm kernel oil, soybean oil, cottonseed oil, and combinations thereof, wherein the oil may be hydrogenated, partially hydrogenated, or non-hydrogenated.

Embodiment 31: The effervescent composition of any one of embodiments 1-30, comprising: up to about 50 dry weight percent of the lipid; up to about 20 dry weight percent of the effervescent material; up to about 50 dry weight percent of the one or more fillers; and from about 1 to about 10 dry weight percent of caffeine.

Embodiment 32: The effervescent composition of any one of embodiments 1-31, wherein the effervescent composition is in granular form, and wherein the composition is enclosed in a pouch to form a pouched product.

Embodiment 33: The effervescent composition of any one of embodiments 1-32, wherein the pouch comprises a fleece material, and wherein the fleece material has at least a portion of the acid component, the base component, or both disposed thereon or impregnated therein.

Embodiment 34: The effervescent composition of any one of embodiments 1-33, in the form of a tablet.

Embodiment 35: The effervescent composition of any one of embodiments 1-33, wherein the tablet has an outer surface, and wherein the effervescent material is disposed on said outer surface.

Embodiment 36: The effervescent composition of any one of embodiments 1-35, wherein the tablet comprises an inner region comprising the lipid.

Embodiment 37: The effervescent composition of any one of embodiments 1-36, wherein the tablet comprises multiple layers comprising: an effervescent layer comprising the effervescent material; and at least one non-effervescent layer.

Embodiment 38: The effervescent composition of any one of embodiments 1-37, wherein the effervescent composition comprises isomalt in an amount of from about 22 to about 33% by weight, based on the total weight of the composition; a glucose- and starch-derived polysaccharide blend in an amount of from about 30 to about 45% by weight, based on the total weight of the composition; a sweetener in an amount of from about 0.1 to about 0.5% by weight, based on the total weight of the composition; L-theanine in an amount of from about 3 to about 5% by weight, based on the total weight of the composition; gamma aminobutyric acid in an amount of from about 4 to about 6% by weight, based on the total weight of the composition; lemon balm extract in an amount of from about 2 to about 8% by weight, based on the total weight of the composition; tartaric acid in an amount of from about 4 to about 6% by weight, based on the total weight of the composition; citric acid in an amount of from about 4 to about 6% by weight, based on the total weight of the composition; sodium bicarbonate in an amount of from about 8 to about 15% by weight, based on the total weight of the composition; a salt in an amount of from about 0.1 to about 0.5% by weight, based on the total weight of the composition; and optionally, a processing aid.

Embodiment 39: The effervescent composition of any one of embodiments 1-37, wherein the effervescent composition comprises isomalt in an amount of from about 20 to about 30% by weight, based on the total weight of the composition; a glucose- and starch-derived polysaccharide blend in an amount of from about 30 to about 45% by weight, based on the total weight of the composition; a sweetener in an amount of from about 0.1 to about 0.5% by weight, based on the total weight of the composition; caffeine in an amount of from about 3 to about 5% by weight, based on the total weight of the composition; taurine in an amount of from about 4 to about 6% by weight, based on the total weight of the composition; vitamin C in an amount of from about 4 to about 6% by weight, based on the total weight of the composition; tartaric acid in an amount of from about 4 to about 6% by weight, based on the total weight of the composition; citric acid in an amount of from about 4 to about 6% by weight, based on the total weight of the composition; sodium bicarbonate in an amount of from about 8 to about 15% by weight, based on the total weight of the composition; a salt in an amount of from about 0.1 to about 0.5% by weight, based on the total weight of the composition; and optionally, a processing aid.

Embodiment 40: The effervescent composition of any one of embodiments 1-37, wherein the effervescent composition comprises isomalt in an amount of from about 22 to about 35% by weight, based on the total weight of the composition; a glucose and starch-derived polysaccharide blend in an amount of from about 28 to about 43% by weight, based on the total weight of the composition; a sweetener in an amount of from about 0.1 to about 0.5% by weight, based on the total weight of the composition; caffeine in an amount of from about 3 to about 5% by weight, based on the total weight of the composition; L-theanine in an amount of from about 4 to about 6% by weight, based on the total weight of the composition; citicoline or sunflower lecithin in an amount of from about 0.5 to about 1.5% by weight, based on the total weight of the composition; sodium citrate in an amount of from about 0.5 to about 1.5% by weight, based on the total weight of the composition; tartaric acid in an amount of from about 4 to about 6% by weight, based on the total weight of the composition; citric acid in an amount of from about 4 to about 6% by weight, based on the total weight of the composition; sodium bicarbonate in an amount of from about 8 to about 15% by weight, based on the total weight of the composition; a salt in an amount of from about 0.1 to about 0.5% by weight, based on the total weight of the composition; and optionally, a processing aid.

Embodiment 41: The effervescent composition of any one of embodiments 1-40, wherein the effervescent composition is in granular form, wherein the effervescent composition is enclosed in a pouch to form a pouched product.

Embodiment 42: The effervescent composition of any one of embodiments 1-441, wherein the pouch comprises a fleece material, and wherein the fleece material has at least a portion of the acid component, the base component, or both disposed thereon or impregnated therein.

Embodiment 43: The effervescent composition of any one of embodiments 1-42, wherein effervescent composition is in the form of a tablet.

Embodiment 44: The effervescent composition of any one of embodiments 1-43, wherein the tablet has an outer surface, and wherein the effervescent layer is disposed on said outer surface.

Embodiment 45: The effervescent composition of any one of embodiments 1-44, wherein tablet comprises an inner region comprising the lipid.

Embodiment 46: The effervescent composition of any one of embodiments 1-45, wherein the tablet comprises multiple layers comprising: an effervescent layer comprising the effervescent material; and at least one non-effervescent layer.

These and other features, aspects, and advantages of the disclosure will be apparent from a reading of the following detailed description together with the accompanying drawing, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

Figure 1A:
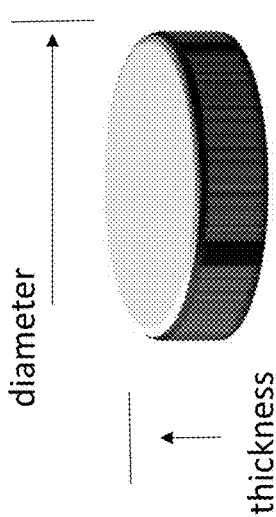

Having thus described aspects of the disclosure in the foregoing general terms, reference will now be made to the accompanying drawing, which is not necessarily drawn to scale. The drawing is exemplary only, and should not be construed as limiting the disclosure.

Figure 1B:
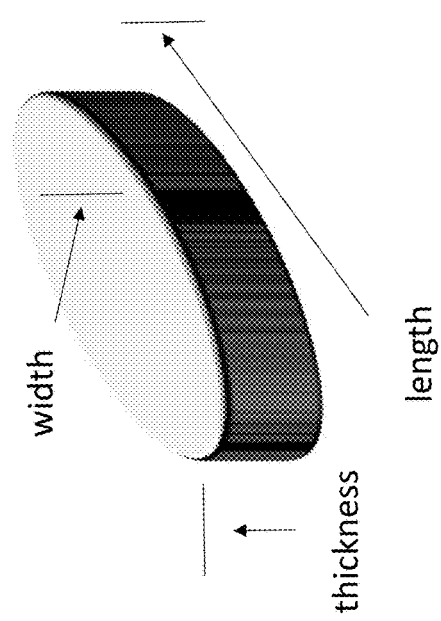
Figure 1C:
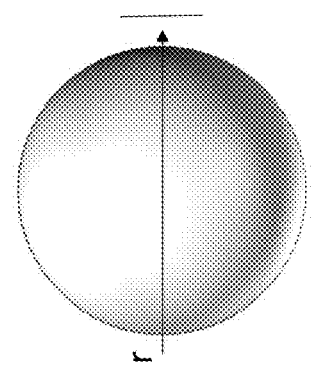
Figure 2:
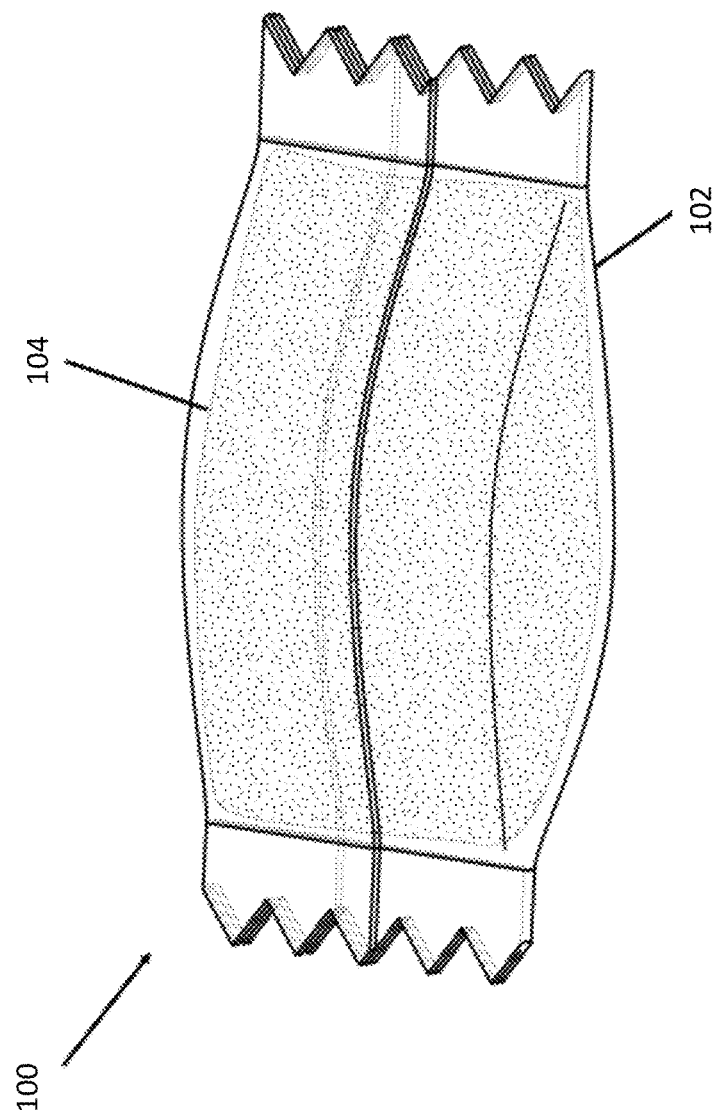
Figure 3C:
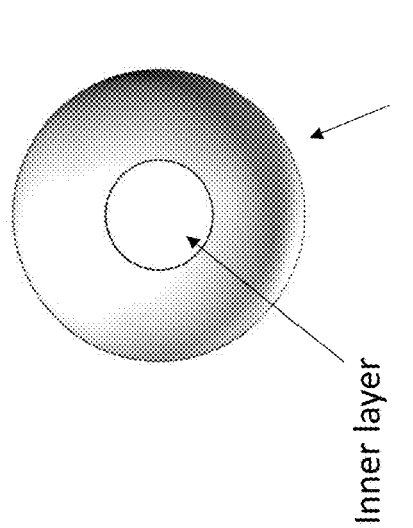
Figure 3B:
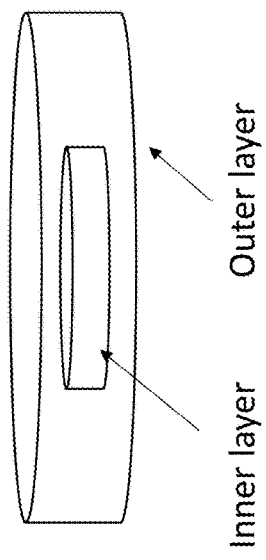
Figure 3A:
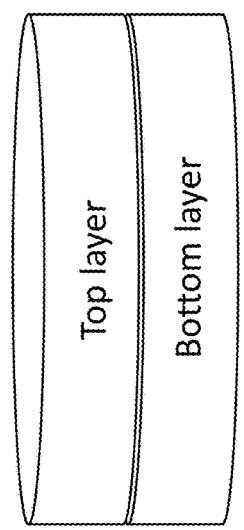

FIG. 1A is a perspective view of an example embodiment of an effervescent composition of the present disclosure in the form of a tablet having a diameter and a thickness;

FIG. 1B is a perspective view of another example embodiment of an effervescent composition of the present disclosure in the form of a tablet having a width, length, and thickness;

FIG. 1C is a perspective view of an example embodiment of an effervescent composition of the present disclosure in the form of a spherical pellet having a diameter;

FIG. 2 is a perspective view of a pouched product embodiment according to an example embodiment of the present disclosure including a pouch or fleece at least partially filled with an effervescent composition for oral use;

FIG. 3A is a perspective view of an example embodiment of an effervescent composition the present disclosure in the form of a layered tablet having a top and bottom layer, wherein at least one of the layers comprises the effervescent composition;

FIG. 3B is a perspective view of an example embodiment of an effervescent composition the present disclosure in the form of a layered tablet having an inner and an outer layer, wherein at least one of the layers comprises the effervescent composition; and FIG. 3C is a cross sectional view of an example embodiment of an effervescent composition of the present disclosure in the form of a spherical pellet having an inner and an outer layer, wherein at least one of the layers comprises the effervescent composition.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements.

As used in this specification and the claims, the singular forms "a," "an," and "the" include plural referents unless the context clearly dictates otherwise.

The term "about" used throughout this specification is used to describe and account for small fluctuations. For example, the term "about" can refer to less than or equal to ±10%, such as less than or equal to ±5%, less than or equal to ±2%, less than or equal to ±1%, less than or equal to ±0.5%, less than or equal to ±0.2%, less than or equal to ±0.1% or less than or equal to ±0.05%. All numeric values herein are modified by the term "about," whether or not explicitly indicated. A value modified by the term "about" of course includes the specific value. For instance, "about 5.0" must include 5.0.

Reference to "dry weight percent" or "dry weight basis" refers to weight on the basis of dry ingredients (i.e., all ingredients except water). Reference to "wet weight" refers to the weight of the effervescent composition including water. Unless otherwise indicated, reference to "weight percent" of a composition reflects the total wet weight of the composition (i.e., including water).

The present disclosure provides an effervescent composition adapted for oral use, comprising an effervescent material capable of causing effervescence in the oral cavity. Surprisingly, it has been found according to the present disclosure that the presence of an effervescent effect in the oral cavity reduces the perception of bitterness associated with certain active ingredients which may be present in a composition adapted for oral use. The effervescent composition as described herein comprises an effervescent material; one or more fillers; a flavoring agent, an active ingredient, or both; and, optionally, a lipid. The relative amounts of the various components within the effervescent composition may vary, and typically are selected so as to provide the desired sensory and performance characteristics to the product. The example individual components of the effervescent composition are described herein below.

Effervescent Material

As used herein, the term "effervescent material" refers to a material which, upon contact with moisture (e.g., saliva in the oral cavity of a consumer of the effervescent composition as disclosed herein), releases bubbles of a gas resulting in a foaming or fizzing action.

In some embodiments, the effervescent material is a combination of two or more components capable of reacting, typically in an aqueous environment, to produce a gas. The resulting gas is typically carbon dioxide, although it is possible to use reactive couples that produce other gases that are safe for human consumption, such as oxygen. The presence of the effervescent materials adds distinctive organoleptic properties to the product, particularly in terms of taste and mouthfeel. In particular, the presence of effervescent materials masks or alters the perception of bitterness, for example, of an active ingredient present in the composition.

The use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; and U.S. Pat. No. 7,381,667 to Bergquist et al., as well as US Pat. Pub. Nos. 2006/0191548 to Strickland et al.; 2009/0025741 to Crawford et al; 2010/0018539 to Brinkley et al.; and 2010/0170522 to Sun et al.; and PCT WO 97/06786 to Johnson et al., all of which are incorporated by reference herein.

In certain embodiments, the effervescent material can include an acid/base pair that provides the effervescent effect of the composition. See, for example, the use of acids and bases in effervescent compositions described in U.S. Pat. Pub. No. 2012/0055494 to Hunt et al., which is incorporated by reference herein.

In one embodiment, the effervescent material is a reactive couple comprising at least one acid component (an acid, an anhydride, or an acid salt) and at least one base capable of reacting with the acid component to release carbon dioxide. Multiple acids and multiple bases can be combined in the same product to produce the desired reaction.

Acid Component

In certain embodiments, the acid component of the effervescent material is selected from carboxylic acids having about 2 to about 12 carbon atoms (e.g., $C_2$-$C_{10}$ or $C_2$-$C_8$ or $C_2$-$C_6$ carboxylic acids), wherein the carboxylic acids are monoprotic or polyprotic (e.g., dicarboxylic acids or tricarboxylic acids). Exemplary organic acids include citric acid, malic acid, tartaric acid, succinic acid, adipic acid, fumaric acid, gluconic acid, and combinations thereof. Example acid salts include acidic sodium salts, acidic calcium salts, dihydrogen phosphate salts, and disodium dihydrogen pyrophosphate salts. In some embodiments, the acid component is citric acid or tartaric acid.

In some embodiments, a combination of acids is utilized where at least one acid is a polyprotic acid, such as a dicarboxylic acid (tartaric acid) or a tricarboxylic acid (e.g., citric acid). Combinations of a dicarboxylic acid and a tricarboxylic acid are also suitable for use in the effervescent material. In some embodiments, the acid component comprises a combination of a tricarboxylic acid and a dicarboxylic acid in a weight ratio of from about 2:1 to about 1:2, for example, from about 2:1, about 1.5:1, or about 1:1, to about 1:1.5, or about 1:2. In some embodiments, the acid component is a combination of citric acid and tartaric acid in a ratio of from about 2:1 to about 1:2 by weight. In specific embodiments, the acid component is a combination of citric acid and tartaric acid in a 1:1 ratio by weight.

The amount of acid component of the effervescent material in the composition can vary, but is typically from about 1 to about 25 dry weight percent, such as about 5 to about 20 dry weight percent, or about 10 to about 18 dry weight percent (e.g., about 10, about 11, about 12, about 13, about 14, about 15, about 16, about 17, or about 18 dry weight percent). Where three or more acids are utilized, each acid is typically present in an amount of about 10 to about 35 dry weight percent, based on the total weight of the acid component. In one embodiment, the acid component is 5% by weight of citric acid and 5% by weight tartaric acid. The acid component, e.g., citric and/or tartaric acid particles, may be encapsulated or coated.

Base Component

Examples of suitable base components include carbonate and bicarbonate materials, particularly alkali metal or alkaline earth metal salts thereof. Carbonate and bicarbonate base materials capable of use in the present invention include sodium carbonate, sodium bicarbonate, potassium carbonate, potassium bicarbonate, magnesium carbonate, calcium carbonate, sodium sesquicarbonate, sodium glycine carbonate, lysine carbonate, and arginine carbonate. In some embodiments, the base component is sodium bicarbonate. The base component, e.g., sodium bicarbonate particles may be encapsulated or coated. Encapsulated sodium bicarbonate is available from, for example Watson (301 Heffernan Drive West Haven, CT 06516) or Clabber Girl Corporation (900 Wabash Ave, Terre Haute, IN 47807).

In some embodiments, a combination of carbonate salts and bicarbonate components may be used. Bicarbonate materials, while highly reactive in effervescent reactions, are not efficient buffering agents in certain desirable pH ranges. Thus, in certain embodiments utilizing both a bicarbonate and carbonate material, it is advantageous to stoichiometrically match the bicarbonate amount to the acid component of the effervescent material and use a carbonate material as the main buffering agent. In this manner, although the carbonate material would be expected to participate in the effervescent reaction to a limited degree, the bicarbonate material is present in an amount sufficient to fully react with the available acid component and the carbonate material is present in an amount sufficient to provide the desired pH range.

The amount of the base component (e.g., carbonate or bicarbonate materials) of the effervescent material in the effervescent composition can vary, but is typically about 4 to about 30 dry weight percent, for example, from about 5 to about 25 dry weight percent, about 8 to about 20 dry weight percent, or about 6 to about 12 dry weight percent (e.g., about 4, about 6, about 8, about 10, about 12, about 14, about 16, about 18, or about 20 dry weight percent). In certain embodiments, the effervescent composition may include both a carbonate component and a bicarbonate component. For such embodiments, the amount of carbonate material can vary, but is typically about 3 to about 20 dry weight percent, such as about 5 to about 15 dry weight percent, or about 8 to about 15 dry weight percent (e.g., about 8, about 9, about 10, about 11, about 12, about 13, or about 14 dry weight percent). For such embodiments, the amount of bicarbonate material can vary, but is typically about 3 to about 20 dry weight percent, often about 5 to about 15 dry weight percent, and most often about 8 to about 15 dry weight percent (e.g., about 8, about 9, about 10, about 11, about 12, about 13, or about 14 dry weight percent). In some embodiments, the base component is sodium bicarbonate, present in an amount by weight of about 12%, based on the total weight of the effervescent composition.

In certain embodiments, it is desirable for the reaction between the acid and base component to proceed completely. To ensure this result, the relevant amount of acid and base can be adjusted so that the necessary equivalent amounts are present. In some embodiments, the acid component and the base component are present in about a 1:1 molar ratio. For example, if a dicarboxylic acid is used, then either a di-reactive base can be used in roughly equivalent amount or a mono-reactive base could be used at a level roughly twice that of the acid. Likewise, if a tricarboxylic acid is used, then either a tri-reactive base can be used in roughly equivalent amount or a mono-reactive base could be used at a level roughly thrice that of the acid. Alternatively, an excess amount of either acid or base can be used, particularly where the acid or base is intended to provide an independent effect on the organoleptic properties of the effervescent composition beyond simply providing effervescence.

The amount of total effervescent material (i.e., all reactive materials that produce the gaseous product) in the effervescent composition can vary. The amount of such material should be sufficient to enable the effervescent composition to effervesce when placed in the oral cavity. The amount of effervescent material is typically about 5 to about 50 dry weight percent, for example, from about 8 to about 30 dry weight percent, about 10 to about 25 dry weight percent (e.g., about 10, about 12, about 14, about 16, about 18, about 20, or about 22 dry weight percent), based on the total weight of the effervescent composition. The amount of effervescent material in some embodiments can be characterized as at least about 10 dry weight percent, or at least about 15 dry weight percent, or at least about 20 dry weight percent, or at least about 25 dry weight percent. The amount of effervescent material in some embodiments can be characterized as no more than about 50 dry weight percent, no more than about 40 dry weight percent, no more than about 35 dry weight percent, no more than about 30 dry weight percent, or no more than about 20 dry weight percent.

The amount of gas (e.g., carbon dioxide) that evolves from the effervescence reaction in the effervescent composition can vary, and depends in part on the desired sensory characteristics of the effervescent composition. The amount of effervescent material can be selected to achieve the desired level of carbon dioxide release. One method for measuring the amount of carbon dioxide released from a given quantity of effervescent composition involves the following steps: (1) pipetting 1 ml of water to a vial; (2) capping the vial; (3) pre-weighing the capped vial using, for example, a Mettler Model AE163 balance or equivalent analytical balance readable to 0.0001 g; (4) reweighing the capped vial along with the effervescent composition to be tested; (5) add the effervescent composition to the water in the vial and cap the vial loosely (tighten cap until barely tight and then loosen cap slightly); (6) after about thirty minutes, vortexing the vials for 3-4 seconds using a vortex mixer such as a Fisher Scientific Touch Mixer Model 232 or equivalent; (8) loosening cap to release trapped gas and then again capping vial loosely; (9) after about one hour, repeating Steps 7 and 8 and reweighing vial; and (10) after about 1.5 hours, repeat Steps 7 and 8 and reweighing vial. The amount of carbon dioxide evolved from the effervescent composition is the difference in weight between Step 4 to Step 10.

In the above test, the intent is to use enough water in the vial to initiate the reaction between acid and base, but not so much that an appreciable amount of carbon dioxide remains dissolved in the water. Vortexing the sample agitates the liquid to overcome supersaturation of the water with carbon dioxide. The vials are loosely capped to allow carbon dioxide to escape without allowing water to evaporate. Carbon dioxide is heavier than air, so weights at different time points are taken to make sure that the carbon dioxide has diffused out of the head space of the vial. The last two vial weights should agree within about 1.5 mg.

The amount of evolved carbon dioxide from an effervescent composition of the invention can be expressed as a ratio of weight of carbon dioxide evolved to total effervescent composition weight. In certain embodiments, this ratio can be from about 10 $\mu$g carbon dioxide/mg of effervescent composition to about 120 $\mu$g carbon dioxide/mg of effervescent composition, from about 10 $\mu$g carbon dioxide/mg to about 60 $\mu$g carbon dioxide/mg, or from about 10 $\mu$g carbon dioxide/mg to about 30 $\mu$g carbon dioxide/mg. In certain embodiments, the amount of evolved carbon dioxide can be characterized as at least about 10 $\mu$g carbon dioxide/mg of effervescent composition, or at least about 15 $\mu$g carbon dioxide/mg of effervescent composition.

Particulate Material

In some embodiments, any one or more components of the effervescent composition, and the overall effervescent composition disclosed herein, can be described as a particulate material. As used herein, the term "particulate" refers to a material in the form of a plurality of individual particles, some of which can be in the form of an agglomerate of multiple particles, wherein the particles have an average length to width ratio less than 2:1, such as less than 1.5:1, such as about 1:1. In various embodiments, the particles of a particulate material can be described as substantially spherical or granular.

The particle size of a particulate material may be measured by sieve analysis. As the skilled person will readily appreciate, sieve analysis (otherwise known as a gradation test) is a method used to measure the particle size distribution of a particulate material. Typically, sieve analysis involves a nested column of sieves which comprise screens, preferably in the form of wire mesh cloths. A pre-weighed sample may be introduced into the top or uppermost sieve in the column, which has the largest screen openings or mesh size (i.e. the largest pore diameter of the sieve). Each lower sieve in the column has progressively smaller screen openings or mesh sizes than the sieve above. Typically, at the base of the column of sieves is a receiver portion to collect any particles having a particle size smaller than the screen opening size or mesh size of the bottom or lowermost sieve in the column (which has the smallest screen opening or mesh size).

In some embodiments, the column of sieves may be placed on or in a mechanical agitator. The agitator causes the vibration of each of the sieves in the column. The mechanical agitator may be activated for a pre-determined period of time in order to ensure that all particles are collected in the correct sieve. In some embodiments, the column of sieves is agitated for a period of time from 0.5 minutes to 10 minutes, such as from 1 minute to 10 minutes, such as from 1 minute to 5 minutes, such as for approximately 3 minutes. Once the agitation of the sieves in the column is complete, the material collected on each sieve is weighed. The weight of each sample on each sieve may then be divided by the total weight in order to obtain a percentage of the mass retained on each sieve. As the skilled person will readily appreciate, the screen opening sizes or mesh sizes for each sieve in the column used for sieve analysis may be selected based on the granularity or known maximum/minimum particle sizes of the sample to be analysed. In some embodiments, a column of sieves may be used for sieve analysis, wherein the column comprises from 2 to 20 sieves, such as from 5 to 15 sieves. In some embodiments, a column of sieves may be used for sieve analysis, wherein the column comprises 10 sieves. In some embodiments, the largest screen opening or mesh sizes of the sieves used for sieve analysis may be 1000 μm, such as 500 μm, such as 400 μm, or such as 300 μm.

In some embodiments, any material referenced herein (e.g., filler, effervescent material, active ingredient, and the overall effervescent composition) has particles with a particle size as measured by sieve analysis of no greater than about 1000 μm, such as no greater than about 500 μm, such as no greater than about 400 μm, such as no greater than about 350 μm, such as no greater than about 300 μm, such as no greater than about 250 μm, such as no greater than about 200 μm, such as no greater than about 150 μm, such as no greater than about 100 μm, such as no greater than about 50 μm, such as no greater than about 40 μm, such as no greater than about 30 μm. In some embodiments, at least 60% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm, such as no greater than about 250 μm, such as no greater than about 200 μm, such as no greater than about 150 μm, such as no greater than about 100 μm, such as no greater than about 50 μm, such as no greater than about 40 μm, such as no greater than about 30 μm. In some embodiments, at least 70% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm, such as no greater than about 250 μm, such as no greater than about 200 μm, such as no greater than about 150 μm, such as no greater than about 100 μm, such as no greater than about 50 μm, such as no greater than about 40 μm, such as no greater than about 30 μm. In some embodiments, at least 80% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm, such as no greater than about 250 µm, such as no greater than about 200 µm, such as no greater than about 150 µm, such as no greater than about 100 µm, such as no greater than about 50 µm, such as no greater than about 40 µm, such as no greater than about 30 µm. In some embodiments, at least 90% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm, such as no greater than about 250 µm, such as no greater than about 200 µm, such as no greater than about 150 µm, such as no greater than about 100 µm, such as no greater than about 50 µm, such as no greater than about 40 µm, such as no greater than about 30 µm. In some embodiments, at least 95% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm, such as no greater than about 250 µm, such as no greater than about 200 µm, such as no greater than about 150 µm, such as no greater than about 100 µm, such as no greater than about 50 µm, such as no greater than about 40 µm, such as no greater than about 30 µm. In some embodiments, at least 99% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm, such as no greater than about 250 µm, such as no greater than about 200 µm, such as no greater than about 150 µm, such as no greater than about 100 µm, such as no greater than about 50 µm, such as no greater than about 40 µm, such as no greater than about 30 µm. In some embodiments, approximately 100% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm, such as no greater than about 250 µm, such as no greater than about 200 µm, such as no greater than about 150 µm, such as no greater than about 100 µm, such as no greater than about 50 µm, such as no greater than about 40 µm, such as no greater than about 30 µm.

In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 0.01 µm to about 1000 µm, such as from about 0.05 µm to about 750 µm, such as from about 0.1 µm to about 500 µm, such as from about 0.25 µm to about 500 µm. In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 10 µm to about 400 µm, such as from about 50 µm to about 350 µm, such as from about 100 µm to about 350 µm, such as from about 200 µm to about 300 µm.

In some embodiments, the effervescent material has a particle size as measured by sieve analysis of less than about 180 µm, such as less than about 150, less than about 120, less than about 80, less than about 60 µm, or less than about 40 µm. In some embodiments, the effervescent material has a particle size as measured by sieve analysis from about 30 to about 180 µm, such as from about 30 to about 40 µm, or from about 50 to about 60 µm. Without wishing to be bound by theory, it is believed that effervescent material particle sizes greater than about 180 µm contribute an unpleasantly rough texture to the effervescent composition. Conversely, effervescent material particle sizes smaller than about 180 µm produce, in some embodiments, a faster onset of effervescence, and provide a smoother texture.

In some embodiments, the particle size as measured by sieve analysis of the remaining effervescent composition components which may be present (e.g., filler, active ingredients, flavorants, sweeteners, taste modifiers, salts, binders, buffering agents, colorants, humectants, oral care additives, preservatives, disintegration aids, antioxidants, flow aids, compressibility aids) is less than about 50 µm, such as less than about 40 µm, less than about 35 µm, or less than about 30 µm. In some embodiments, the particle size as measured by sieve analysis of the remaining effervescent composition components which may be present is from about 25, about 30, or about 35, to about 40, about 45, or about 50 µm. In some embodiments, the particle size as measured by sieve analysis of the remaining effervescent composition components which may be present is from about 25 to about 35 µm. In some embodiments, the particle size as measured by sieve analysis of the remaining effervescent composition components which may be present is less than about 32 µm.

Gasified Material

In certain embodiments, the effervescence may be produced by release of entrapped gas rather than by chemical reaction. Accordingly, in some embodiments, the effervescent material comprises a sugar material containing an entrapped gaseous component, such that release of the entrapped gaseous component occurs upon dissolution of the sugar material in the oral cavity. In some embodiments, the sugar material containing an entrapped gaseous component is in the form of a gasified sugar material in particulate form, the gasified sugar material particles being in admixture with the filler and active ingredient. As used herein, "gasified sugar material" refers to a sugar material containing an entrapped gaseous component capable of release upon dissolution of the sugar material in the oral cavity. The gasified sugar material is typically provided in solid form (e.g., granular or particulate form). The average particle size of the gasified sugar material can vary, but is typically about 50 to about 800 microns, more often about 100 to about 600 microns, and most often about 125 to about 500 microns. The gasified sugar material is advantageously maintained in a very dry state to avoid premature effervescence during handling or storage. For example, the gasified sugar material will typically comprise less than about 5% water by weight, less than about 3% water by weight, less than about 2% water by weight, or less than about 1% water by weight.

Commercially available examples of gasified sugar material are sold under the brand name Carbonated Crystals™ by Raven Manufacturing, LLC of Neenah, Wis. Exemplary methods for forming gasified sugar materials are set forth in U.S. Pat. No. 4,289,794 to Kleiner et al.; U.S. Pat. No. 5,165,951 to Gallart et al., and U.S. Pat. No. 5,439,698 to Ahn et al, all of which are incorporated by reference herein. Typical manufacturing processes involve introducing a gaseous component (e.g., carbon dioxide) under pressure (e.g., 50 to 650 psig) to the sugar material while the sugar is in melted form.

The amount of gasified sugar material in the effervescent composition can vary, and will depend in part on the desired organoleptic properties of the effervescent composition. Typically, the amount of gasified sugar material (including the total weight of sugar materials and entrapped gas) is in the range of about 10 to about 90 dry weight percent, based on the total weight of the effervescent composition, such as about 20 to about 60 dry weight percent, or about 30 to about 50 dry weight percent.

The sugar component of the gasified sugar material can be any of a variety of monosaccharides (e.g., glucose, fructose, galactose), disaccharides (e.g., sucrose, lactose, maltose), trisaccharides, or oligosaccharides. Although sucrose or other nutritive sweeteners can be used as the sugar material, the effervescent composition of the disclosure can also be prepared as a sugar-free product, meaning the gasified sugar material can be characterized as a sugar substitute. "Sugar-free" as used herein is intended to include products having less than about 1/15th sugar by weight, or less than about 1/10th sugar by weight.

Filler

Effervescent compositions as described herein include one or more fillers. Such fillers may fulfill multiple functions, such as enhancing certain organoleptic properties such as texture and mouthfeel, enhancing cohesiveness or compressibility of the product, and the like. Generally, the fillers are porous particulate materials and are cellulose-based. For example, suitable fillers are any non-tobacco plant material or derivative thereof, including cellulose materials derived from such sources. Examples of cellulosic non-tobacco plant material include cereal grains (e.g., maize, oat, barley, rye, buckwheat, and the like), sugar beet (e.g., FIBREX® brand filler available from International Fiber Corporation), bran fiber, and mixtures thereof. Non-limiting examples of derivatives of non-tobacco plant material include starches (e.g., from potato, wheat, rice, corn), natural cellulose, and modified cellulosic materials.

"Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the effervescent composition based on the ability of the starch material to impart a specific organoleptic property to the effervescent composition. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, canna, chestnuts, colacasia, katakuri, kudzu, malanga, millet, oats, oca, Polynesian arrowroot, sago, sorghum, sweet potato, quinoa, rye, tapioca, taro, tobacco, water chestnuts, and yams. Certain starches are modified starches. A modified starch has undergone one or more structural modifications, often designed to alter its high heat properties. Some starches have been developed by genetic modifications, and are considered to be "modified" starches. Other starches are obtained and subsequently modified. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, enzyme treatment, acetylation, hydroxypropylation, and/or partial hydrolysis. Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl distarch glycerol, and starch sodium octenyl succinate.

Combinations of fillers can also be used. For example, in some embodiments, the one or more fillers comprise a mixture of glucose and starch-derived polysaccharides. One such suitable mixture of glucose and starch-derived polysaccharides is EMDEX®, available from JRS PHARMA LP, USA, 2981 Route 22, Patterson, NY 12563-2359.

In some embodiments, the filler comprises a cellulose material or a cellulose derivative, such as microcrystalline cellulose ("mcc"). The mcc may be synthetic or semi-synthetic, or it may be obtained entirely from natural celluloses. The mcc may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof.

Additional examples of potential fillers include maltodextrin, dextrose, calcium carbonate, calcium phosphate, lactose, and sugar alcohols. In some embodiments, the one or more fillers includes at least one sugar alcohol. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). In some embodiments, the one or more fillers comprise at least one of mannitol, maltodextrin, isomalt, and starch-derived polysaccharides. In some embodiments, one or more fillers comprise mannitol. In some embodiments, the one or more fillers comprise isomalt. In some embodiments, the one or more fillers is a combination of mannitol and maltodextrin. In some embodiments, the one or more fillers comprises isomalt, glucose, and starch-derived polysaccharides. In some embodiments, the one or more fillers comprises EMDEX®. In some embodiments, the one or more fillers comprises a combination of isomalt and EMDEX®.

The amount of filler can vary, but is typically greater than about 25%, and up to about 75% of the effervescent composition by weight, based on the total weight of the composition. A typical range of filler within the effervescent composition can be from about 25 to about 75% by total weight of the effervescent composition, for example, from about 25, about 30, about 35, about 40, about 45, or about 50%, to about 55, about 60%, about 65, about 70%, or about 75% by weight (e.g., about 20 to about 50%, or about 25 to about 45% by weight). In certain embodiments, the amount of filler is at least about 30% by weight, such as at least about 35%, or at least about 35%, or at least about 40%, or at least about 45%, or at least about 50%, based on the total weight of the effervescent composition. In some embodiments, the one or more fillers are present in a total amount of up to about 50% by weight, based on the total weight of the effervescent composition. In some embodiments, the one or more fillers are present in a total amount of at least about 30% by weight, based on the total weight of the effervescent composition. In particular embodiments, the one or more fillers includes at least one sugar alcohol. In particular embodiments, the one or more fillers comprises from about 25 to about 35% of isomalt and from about 30 to about 45% of EMDEX®.

Lipid

In some embodiments, the effervescent composition comprises a lipid. Such compositions may, in some embodiments, be described as "meltable" or "melting" effervescent compositions. The lipid of the effervescent composition is typically a fat, oil, or wax substance derived from animal or plant material (e.g., plant-derived fats), and typically comprises mostly triglycerides along with lesser amounts of free fatty acids and mono- or diglycerides. In certain embodiments, the lipid is a solid or semi-solid at room temperature (i.e., 25° C.) and capable of at least partially liquefying when subjected to the temperature of the oral cavity of the user (i.e., "melting"). Example plant-derived fats are comprised primarily of saturated or unsaturated fatty acid chains (most of which are bound within triglyceride structures) having a carbon length of about 10 to about 26 carbon atoms, or about 14 to about 20 carbon atoms, or about 14 to about 18 carbon atoms.

In some embodiments, the lipid comprises an oil and, in particular, a food grade oil. Such oils include, but are not limited to, vegetable oils (e.g., acai oil, almond oil, amaranth oil, apricot oil, apple seed oil, argan oil, avocado oil, babassu oil, beech nut oil, ben oil, bitter gourd oil, black seed oil, blackcurrant seed oil, borage seed oil, borneo tallow nut oil, bottle gourd oil, brazil nut oil, buffalo gourd oil, butternut squash seed oil, cape chestnut oil, canola oil, carob cashew oil, cocoa butter, cocklebur oil, coconut oil, corn oil, cothune oil, coriander seed oil, cottonseed oil, date seed oil, dika oil, egus seed oil, evening primrose oil, false flax oil, flaxseed oil, grape seed oil, grapefruit seed oil, hazelnut oil, hemp oil, kapok seed oil, kenaf seed oil, lallemantia oil, lemon oil, linseed oil, macadamia oil, mafura oil, manila oil, meadowfoam seed oil, mongongo nut oil, mustard oil, niger seed oil, nutmeg butter, okra seed oil, olive oil, orange oil, palm oil, palm stearin, papaya seed oil, peanut oil, pecan oil, perilla seed oil, persimmon seed oil, pequi oil, pili nut oil, pine nut oil, pistachio oil, pomegranate seed oil, poppyseed oil, pracaxi oil, prune kernel oil, pumpkin seed oil, quinoa oil, ramtil oil, rapeseed oil, rice bran oil, royle oil, sacha inchi oil, safflower oil, sapote oil, seje oil, sesame oil, shea butter, soybean oil, sunflower oil, taramira oil, tea seed oil, thistle oil, tigernut oil, tobacco seed oil, tomato seed oil, walnut oil, watermelon seed oil, wheat germ oil, and combinations thereof), animal oils (e.g., cattle fat, buffalo fat, sheep fat, goat fat, pig fat, lard, camel fat, tallow, liquid margarine, fish oil, fish liver oil, whale oil, seal oil, and combinations thereof), and mineral oils.

In certain embodiments, the plant-derived fats of the present disclosure include palm oil, palm kernel oil, soybean oil, cottonseed oil, and mixtures thereof. In one embodiment, the lipid is a blend of palm oil and palm kernel oil. The lipid can be, for example, hydrogenated, partially hydrogenated, or non-hydrogenated. Example embodiments of lipids can be purchased under the brand names CEBES®, CISAO®, or CONFAO®, available from AarhusKarlshamn USA Inc, and under the brand name Paramount™, available from Bunge Loders Croklaan.

The melting point of the lipid is typically about 29° C. or above, such as about 29° C. to about 49° C., or about 36° C. to about 45° C., or about 38° C. to about 41° C. In some embodiments, use of lipids with a melting point of less than about 36° C. is not advantageous due to possible melting during product storage or handling. One test for determining the melting point of lipids is the Mettler dropping point method (ASTM D3954-15, Standard Test Method for Dropping Point of Waxes, ASTM International, West Conshohocken, PA, 2015, www.astm.org.).

The amount of lipid within the effervescent composition may vary. In certain embodiments, the amount of lipid is at least about 10 percent, at least about 20 percent, or at least about 30 percent, on a dry weight basis of the effervescent composition. In certain embodiments, the amount of lipid is less than about 70 percent, less than about 60 percent, or less than about 50 weight percent, on a dry weight basis. Example lipid weight ranges include about 10 to about 70 dry weight percent, such as about 20 to about 50 dry weight percent. In some embodiments, the amount of lipid is about 20, about 25, about 30, about 35, about 40, about 45, or about 50 percent by weight of the total effervescent composition.

In one embodiment, the effervescent composition is meltable. In one embodiment, the meltable effervescent composition comprises up to about 50 dry weight percent of the lipid; up to about 20 dry weight percent of effervescent material; up to about 50 dry weight percent of the one or more fillers; and from about 1 to about 10 dry weight percent of caffeine. In one embodiment, the effervescent composition comprises about 40% of lipid, about 45% of isomalt, and about 10% of the effervescent material, wherein the effervescent material comprises an acid component and a base component. In a specific embodiment, the acid component is a mixture of citric acid and tartaric acid, and the base component is sodium bicarbonate. In a specific embodiment, the lipid is an oil selected from the group consisting of palm oil, palm kernel oil, soybean oil, cottonseed oil, and combinations thereof, wherein the oil may be hydrogenated, partially hydrogenated, or non-hydrogenated.

Active Ingredient

The effervescent composition as disclosed herein, in certain embodiments, comprises at least one active ingredient. As used herein, an "active ingredient" refers to one or more substances belonging to any of the following categories: API (active pharmaceutical substances), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods". These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Non-limiting examples of active ingredients include those falling in the categories of botanical ingredients, stimulants, amino acids, nicotine components, and/or pharmaceutical, nutraceutical, and medicinal ingredients (e.g., vitamins, such as A, B3, B6, B12, and C, and/or cannabinoids, such as tetrahydrocannabinol (THC) and cannabidiol (CBD)). Each of these categories is further described herein below. The particular choice of active ingredients will vary depending upon the desired flavor, texture, and desired characteristics of the particular product.

The particular percentages of active ingredients present will vary depending upon the desired characteristics of the particular product. Typically, an active ingredient or combination thereof is present in a total concentration of at least about 0.001% by weight of the effervescent composition, such as in a range from about 0.001% to about 20%. In some embodiments, the active ingredient or combination of active ingredients is present in a concentration from about 0.1% w/w to about 10% by weight, such as, e.g., from about from about 0.5% w/w to about 10%, from about 1% to about 10%, or from about 1% to about 5% by weight, based on the total weight of the effervescent composition. In some embodiments, the active ingredient or combination of active ingredients is present in a concentration of from about 0.001%, about 0.01%, about 0.1%, or about 1%, up to about 20% by weight, such as, e.g., from about from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the effervescent composition. Further suitable ranges for specific active ingredients are provided herein below.

Botanical

In some embodiments, the active ingredient comprises a botanical ingredient. As used herein, the term "botanical ingredient" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, bleaching, or other treatment processes capable of altering the physical and/or chemical nature of the material). For the purposes of the present disclosure, a "botanical" includes, but is not limited to, "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species).

When present, a botanical is typically at a concentration of from about 0.01% w/w to about 10% by weight, such as, e.g., from about from about 0.01% w/w, about 0.05%, about 0.1%, or about 0.5%, to about 1%, about 2%, about 3%, about 4%, about 5%, about 6%, about 7%, about 8%, about 9%, or about 10%, about 11%, about 12%, about 13%, about 14%, or about 15% by weight, based on the total weight of the effervescent composition.

The botanical materials useful in the present disclosure may comprise, without limitation, any of the compounds and sources set forth herein, including mixtures thereof. Certain botanical materials of this type are sometimes referred to as dietary supplements, nutraceuticals, "phytochemicals" or "functional foods." Certain botanicals, as the plant material or an extract thereof, have found use in traditional herbal medicine, and are described further herein. Non-limiting examples of botanicals or botanical-derived materials include ashwagandha, Bacopa monniera, baobab, basil, *Centella asiatica*, Chai-hu, chamomile, cherry blossom, chlorophyll, cinnamon, citrus, cloves, cocoa, cordyceps, curcumin, damiana, *Dorstenia arifolia*, *Dorstenia odorata*, essential oils, eucalyptus, fennel, *Galphimia glauca*, ginger, *Ginkgo biloba*, ginseng (e.g., *Panax ginseng*), green tea, *Griffonia simplicifolia*, guarana, hemp, hops, jasmine, *Kaempferia parviflora* (Thai ginseng), kava, lavender, lemon balm, lemongrass, licorice, lutein, maca, matcha, *Nardostachys chinensis*, oil-based extract of *Viola odorata*, peppermint, quercetin, resveratrol, *Rhizoma gastrodiae*, *Rhodiola*, rooibos, rose essential oil, rosemary, *Sceletium tortuosum*, Schisandra, Skullcap, spearmint extract, Spikenard, terpenes, tisanes, turmeric, *Turnera aphrodisiaca*, valerian, white mulberry, and Yerba mate. In some embodiments, the effervescent composition comprises lemon balm extract. In some embodiments, the effervescent composition comprises ginseng.

Stimulants

In some embodiments, the active ingredient comprises one or more stimulants. As used herein, the term "stimulant" refers to a material that increases activity of the central nervous system and/or the body, for example, enhancing focus, cognition, vigor, mood, alertness, and the like. Non-limiting examples of stimulants include caffeine, theacrine, theobromine, and theophylline. Theacrine (1,3,7,9-tetramethyluric acid) is a purine alkaloid which is structurally related to caffeine, and possesses stimulant, analgesic, and anti-inflammatory effects. Present stimulants may be natural, naturally derived, or wholly synthetic. For example, certain botanical materials (guarana, tea, coffee, cocoa, and the like) may possess a stimulant effect by virtue of the presence of e.g., caffeine or related alkaloids, and accordingly are "natural" stimulants. By "naturally derived" is meant the stimulant (e.g., caffeine, theacrine) is in a purified form, outside its natural (e.g., botanical) matrix. For example, caffeine can be obtained by extraction and purification from botanical sources (e.g., tea). By "wholly synthetic", it is meant that the stimulant has been obtained by chemical synthesis. In some embodiments, the active ingredient comprises caffeine. In some embodiments, the active ingredient is caffeine. In some embodiments, the caffeine is present in an encapsulated form. On example of an encapsulated caffeine is Vitashure®, available from Balchem Corp., 52 Sunrise Park Road, New Hampton, NY, 10958.

When present, a stimulant or combination of stimulants (e.g., caffeine, theacrine, and combinations thereof) is typically at a concentration of from about 0.1% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the effervescent composition.

Amino Acids

In some embodiments, the active ingredient comprises an amino acid. As used herein, the term "amino acid" refers to an organic compound that contains amine (—NH$_2$) and carboxyl (—COOH) or sulfonic acid (SO$_3$H) functional groups, along with a side chain (R group), which is specific to each amino acid. Amino acids may be proteinogenic or non-proteinogenic. By "proteinogenic" is meant that the amino acid is one of the twenty naturally occurring amino acids found in proteins. The proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. By "non-proteinogenic" is meant that either the amino acid is not found naturally in protein, or is not directly produced by cellular machinery (e.g., is the product of post-tranlational modification). Non-limiting examples of non-proteinogenic amino acids include gamma-aminobutyric acid (GABA), taurine (2-aminoethanesulfonic acid), theanine (L-γ-glutamylethylamide), hydroxyproline, and beta-alanine. In some embodiments, the effervescent composition comprises an amino acid selected from one or more of arginine, beta-alanine, carnitine, choline, creatine, GABA, glutamic acid, lysine, magnesium threonate, phenylalanine, tryptophan, tyrosine, and combination thereof. In some embodiments, the effervescent composition comprises theanine. In some embodiments, the effervescent composition comprises GABA. In some embodiments, the effervescent composition comprises taurine.

When present, an amino acid or combination of amino acids (e.g., taurine, theanine, GABA, or combinations thereof) is typically at a concentration of from about 0.1% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the effervescent composition.

Vitamins

In some embodiments, the active ingredient comprises a vitamin or combination of vitamins. As used herein, the term "vitamin" refers to an organic molecule (or related set of molecules) that is an essential micronutrient needed for the proper functioning of metabolism in a mammal. There are thirteen vitamins required by human metabolism, which are: vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones). In some embodiments, the active ingredient comprises vitamin C.

When present, a vitamin or combination of vitamins (e.g., vitamin B6, vitamin B12, vitamin E, vitamin C, or a combination thereof) is typically at a concentration of from about 0.01% w/w to about 10% by weight, such as, e.g., from about from about 0.01%, about 0.02%, about 0.03%, about 0.04%, about 0.05%, about 0.06%, about 0.07%, about 0.08%, about 0.09%, about 0.1% w/w, about 0.2%, about 0.3%, about 0.4%, about 0.5% about 0.6%, about 0.7%, about 0.8%, about 0.9%, or about 1%, to about 2%, about 3%, about 4%, about 5%, about 6%, about 7%, about 8%, about 9%, or about 10% by weight, based on the total weight of the effervescent composition.

Nicotine Component

In certain embodiments, the active ingredient comprises a nicotine component. By "nicotine component" is meant any suitable form of nicotine (e.g., free base or salt) for providing oral absorption of at least a portion of the nicotine present. Typically, the nicotine component is selected from the group consisting of nicotine free base and a nicotine salt. In some embodiments, the nicotine component is nicotine in its free base form, which easily can be adsorbed in for example, a microcrystalline cellulose material to form a microcrystalline cellulose-nicotine carrier complex. See, for example, the discussion of nicotine in free base form in US Pat. Pub. No. 2004/0191322 to Hansson, which is incorporated herein by reference.

In some embodiments, at least a portion of the nicotine component can be employed in the form of a salt. Salts of nicotine can be provided using the types of ingredients and techniques set forth in U.S. Pat. No. 2,033,909 to Cox et al. and Perfetti, *Beitrage Tabakforschung Int.*, 12: 43-54 (1983), which are incorporated herein by reference. Additionally, salts of nicotine are available from sources such as Pfaltz and Bauer, Inc. and K&K Laboratories, Division of ICN Biochemicals, Inc. Typically, the nicotine component is selected from the group consisting of nicotine free base, a nicotine salt such as hydrochloride, dihydrochloride, monotartrate, bitartrate, sulfate, salicylate, and nicotine zinc chloride.

In some embodiments, at least a portion of the nicotine can be in the form of a resin complex of nicotine, where nicotine is bound in an ion-exchange resin, such as nicotine polacrilex, which is nicotine bound to, for example, a polymethacrilic acid, such as Amberlite IRP64, Purolite C115HMR, or Doshion P551. See, for example, U.S. Pat. No. 3,901,248 to Lichtneckert et al., which is incorporated herein by reference. Another example is a nicotine-polyacrylic carbomer complex, such as with Carbopol 974P. In some embodiments, nicotine may be present in the form of a nicotine polyacrylic complex.

Typically, the nicotine component (calculated as the free base) when present, is in a concentration of at least about 0.001% by weight of the effervescent composition, such as in a range from about 0.001% to about 10%. In some embodiments, the nicotine component is present in a concentration from about 0.1% w/w to about 10% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the effervescent composition. In some embodiments, the nicotine component is present in a concentration from about 0.1% w/w to about 3% by weight, such as, e.g., from about from about 0.1% w/w to about 2.5%, from about 0.1% to about 2.0%, from about 0.1% to about 1.5%, or from about 0.1% to about 1% by weight, calculated as the free base and based on the total weight of the composition.

In some embodiments, the products or compositions of the disclosure can be characterized as completely free or substantially free of any nicotine component (e.g., any embodiment as disclosed herein may be completely or substantially free of any nicotine component). By "substantially free" is meant that no nicotine has been intentionally added, beyond trace amounts that may be naturally present in e.g., a botanical material. For example, certain embodiments can be characterized as having less than 0.001% by weight of nicotine, or less than 0.0001%, or even 0% by weight of nicotine, calculated as the free base.

In some embodiments, the active ingredient comprises a nicotine component (e.g., any effervescent composition of the disclosure, in addition to comprising any active ingredient or combination of active ingredients as disclosed herein, may further comprise a nicotine component).
Cannabinoids In some embodiments, the active ingredient comprises one or more cannabinoids. As used herein, the term "cannabinoid" refers to a class of diverse natural or synthetic chemical compounds that acts on cannabinoid receptors (i.e., CB1 and CB2) in cells that alter neurotransmitter release in the brain. Cannabinoids are cyclic molecules exhibiting particular properties such as the ability to easily cross the blood-brain barrier. Cannabinoids may be naturally occurring (Phytocannabinoids) from plants such as cannabis, (endocannabinoids) from animals, or artificially manufactured (synthetic cannabinoids). *Cannabis* species express at least 85 different phytocannabinoids, and these may be divided into subclasses, including cannabigerols, cannabichromenes, cannabidiols, tetrahydrocannabinols, cannabinols and cannabinodiols, and other cannabinoids, such as cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabmolic acid (THCA), and tetrahydrocannabivarinic acid (THCV A).

In some embodiments, the cannabinoid is selected from the group consisting of cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabmolic acid (THCA), tetrahydrocannabivarinic acid (THCV A), and mixtures thereof. In some embodiments, the cannabinoid comprises at least tetrahydrocannabinol (THC). In some embodiments, the cannabinoid is tetrahydrocannabinol (THC). In some embodiments, the cannabinoid comprises at least cannabidiol (CBD). In some embodiments, the cannabinoid is cannabidiol (CBD). In some embodiments, the CBD is synthetic CBD. Notably, CBD has a log P value of about 6.5, making it insoluble in an aqueous environment (e.g., saliva).

In some embodiments, the cannabinoid (e.g., CBD) is added to the oral product in the form of an isolate. An isolate is an extract from a plant, such as cannabis, where the active material of interest (in this case the cannabinoid, such as CBD) is present in a high degree of purity, for example greater than 95%, greater than 96%, greater than 97%, greater than 98%, or around 99% purity.

In some embodiments, the cannabinoid is an isolate of CBD in a high degree of purity, and the amount of any other cannabinoid in the oral product is no greater than about 1% by weight of the oral product, such as no greater than about 0.5% by weight of the oral product, such as no greater than about 0.1% by weight of the oral product, such as no greater than about 0.01% by weight of the oral product.

The choice of cannabinoid and the particular percentages thereof which may be present within the disclosed oral product will vary depending upon the desired flavor, texture, and other characteristics of the oral product.

Alternatively, or in addition to the cannabinoid, the active agent may include a cannabimimetic, which is a class of compounds derived from plants other than cannabis that have biological effects on the endocannabinoid system similar to cannabinoids. Examples include yangonin, alpha-amyrin or beta-amyrin (also classified as terpenes), cyanidin, curcumin (tumeric), catechin, quercetin, salvinorin A, N-acylethanolamines, and N-alkylamide lipids. Such compounds can be used in the same amounts and ratios noted herein for cannabinoids.

When present, a cannabinoid (e.g., CBD) is typically in a concentration of at least about 0.1% by weight of the effervescent composition, such as in a range from about 0.1% to about 30%, such as, e.g., from about from about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 15%, about 20%, or about 30% by weight, based on the total weight of the effervescent composition.
Terpenes Active ingredients suitable for use in the present disclosure can also be classified as terpenes, many of which are associated with biological effects, such as calming effects. Terpenes are understood to have the general formula of $(C_5H_8)_n$ and include monoterpenes, sesquiterpenes, and diterpenes. Terpenes can be acyclic, monocyclic or bicyclic in structure. Some terpenes provide an entourage effect when used in combination with cannabinoids or cannabimimetics. Examples include beta-caryophyllene, linalool, limonene, beta-citronellol, linalyl acetate, pinene (alpha or beta), geraniol, carvone, eucalyptol, menthone, iso-menthone, piperitone, myrcene, beta-bourbonene, and germacrene, which may be used singly or in combination.

In some embodiments, the terpene is a terpene derivable from a phytocannabinoid producing plant, such as a plant from the stain of the *Cannabis sativa* species, such as hemp. Suitable terpenes in this regard include so-called "C10" terpenes, which are those terpenes comprising 10 carbon atoms, and so-called "C15" terpenes, which are those terpenes comprising 15 carbon atoms. In some embodiments, the active ingredient comprises more than one terpene. For example, the active ingredient may comprise one, two, three, four, five, six, seven, eight, nine, ten or more terpenes as defined herein. In some embodiments, the terpene is selected from pinene (alpha and beta), geraniol, linalool, limonene, carvone, eucalyptol, menthone, iso-menthone, piperitone, myrcene, beta-bourbonene, germacrene and mixtures thereof.
Pharmaceutical Ingredients In some embodiments, the active ingredient comprises a pharmaceutical ingredient. The pharmaceutical ingredient can be any known agent adapted for therapeutic, prophylactic, or diagnostic use. These can include, for example, synthetic organic compounds, proteins and peptides, polysaccharides and other sugars, lipids, phospholipids, inorganic compounds (e.g., magnesium, selenium, zinc, nitrate), neurotransmitters or precursors thereof (e.g., serotonin, 5-hydroxy-tryptophan, oxitriptan, acetylcholine, dopamine, melatonin), and nucleic acid sequences, having therapeutic, prophylactic, or diagnostic activity. Non-limiting examples of pharmaceutical ingredients include analgesics and antipyretics (e.g., acetylsalicylic acid, acetaminophen, 3-(4-isobutylphenyl)propanoic acid), phosphatidylserine, myo-inositol, docosahexaenoic acid (DHA, Omega-3), arachidonic acid (AA, Omega-6), S-adenosylmethionine (SAM), beta-hydroxy-beta-methylbutyrate (HMB), citicoline (cytidine-5'-diphosphate-choline), and cotinine. In some embodiments, the active ingredient comprises citicoline. In some embodiments, the active ingredient comprises sunflower lecithin.

The amount of pharmaceutical ingredient may vary. For example, when present, a pharmaceutical ingredient is typically at a concentration of from about 0.001% w/w to about 10% by weight, such as, e.g., from about from about 0.01%, about 0.02%, about 0.03%, about 0.04%, about 0.05%, about 0.06%, about 0.07%, about 0.08%, about 0.09%, about 0.1% w/w, about 0.2%, about 0.3%, about 0.4%, about 0.5% about 0.6%, about 0.7%, about 0.8%, about 0.9%, or about 1%, to about 2%, about 3%, about 4%, about 5%, about 6%, about 7%, about 8%, about 9%, or about 10% by weight, based on the total weight of the effervescent composition.

Flavoring Agent

In some embodiments, the effervescent composition as described herein comprises a flavoring agent. As used herein, a "flavoring agent" or "flavorant" is any flavorful or aromatic substance capable of altering the sensory characteristics associated with the oral product. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy. Specific types of flavors include, but are not limited to, vanilla, coffee, chocolate/cocoa, cream, mint, spearmint, menthol, peppermint, wintergreen, eucalyptus, lavender, cardamom, nutmeg, cinnamon, clove, cascarilla, sandalwood, honey, jasmine, ginger, anise, sage, licorice, lemon, orange, apple, peach, lime, cherry, strawberry, pineapple, lemon balm, and any combinations thereof. See also, Leffingwell et al., Tobacco Flavoring for Smoking Products, R. J. Reynolds Tobacco Company (1972), which is incorporated herein by reference. Flavorings also may include components that are considered moistening, cooling or smoothening agents, such as eucalyptus. These flavors may be provided neat (i.e., alone) or in a composite, and may be employed as concentrates or flavor packages (e.g., spearmint and menthol, orange and cinnamon; lime, pineapple, and the like). Representative types of components also are set forth in U.S. Pat. No. 5,387,416 to White et al.; US Pat. App. Pub. No. 2005/0244521 to Strickland et al.; and PCT Application Pub. No. WO 05/041699 to Quinter et al., each of which is incorporated herein by reference. In some instances, the flavoring agent may be provided in a spray-dried form or a liquid form.

The amount of flavoring agent utilized in the effervescent composition can vary, but is typically up to about 10 weight percent, and certain embodiments are characterized by a flavoring agent content of at least about 0.1 weight percent, such as about 0.1 to about 10 weight percent, about 0.3 to about 5 weight percent, or about 0.5 to about 3 weight percent, based on the total dry weight of the effervescent composition.

Sweeteners

In order to improve the sensory properties of the effervescent composition according to the disclosure, one or more sweeteners may be added. The sweeteners can be any sweetener or combination of sweeteners, in natural or artificial form, or as a combination of natural and artificial sweeteners. Examples of natural sweeteners include fructose, sucrose, glucose, maltose, mannose, galactose, lactose, stevia, honey, and the like. Examples of artificial sweeteners include sucralose, isomaltulose, maltodextrin, saccharin, aspartame, acesulfame K, neotame, and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). In some embodiments, the sweetener is xylitol, sucralose, or a combination thereof. In some embodiments, the sweetener is sucralose.

When present, a sweetener or combination of sweeteners may make up from about 0.1 to about 20% or more of the of the effervescent composition by weight, for example, from about 0.1 to about 1%, from about 1 to about 5%, from about 5 to about 10%, or from about 10 to about 20% by weight, based on the total weight of the effervescent composition.

Taste Modifiers

In order to improve the organoleptic properties of an effervescent composition as disclosed herein, the effervescent composition may include one or more taste modifying agents ("taste modifiers") which may serve to mask, alter, block, or improve e.g., the flavor of an effervescent composition as described herein. Non-limiting examples of such taste modifiers include analgesic or anesthetic herbs, spices, and flavors which produce a perceived cooling (e.g., menthol, eucalyptus, mint), warming (e.g., cinnamon), or painful (e.g., capsaicin) sensation. Certain taste modifiers fall into more than one overlapping category.

In some embodiments, the taste modifier modifies one or more of bitter, sweet, salty, or sour tastes. In some embodiments, the taste modifier targets pain receptors. In some embodiments, the effervescent composition comprises an active ingredient having a bitter taste, and a taste modifier which masks or blocks the perception of the bitter taste. In some embodiments, the taste modifier is a substance which targets pain receptors (e.g., vanilloid receptors) in the user's mouth to mask e.g., a bitter taste of another component (e.g., an active ingredient). Suitable taste modifiers include, but are not limited to, capsaicin, gamma-amino butyric acid (GABA), adenosine monophosphate (AMP), lactisole, sodium citrate, or a combination thereof.

When present, a representative amount of taste modifier is about 0.01% by weight or more, about 0.1% by weight or more, or about 1.0% by weight or more, but will typically make up less than about 10% by weight of the total weight of the effervescent composition, (e.g., from about 0.01%, about 0.05%, about 0.1%, or about 0.5%, to about 1%, about 5%, or about 10% by weight of the total weight of the effervescent composition).

Salts

In some embodiments, the effervescent composition comprises a salt (e.g., an alkali metal salt), typically employed in an amount sufficient to provide desired sensory attributes to the effervescent composition. In some embodiments, certain salts may also serve as electrolytes or act in synergy with electrolytes. For example, without wishing to be bound by theory, sodium citrate may provide both a source of sodium (electrolyte) as well as aid in the absorption of other electrolytes and water. Non-limiting examples of suitable salts include sodium chloride, potassium chloride, ammonium chloride, flour salt, sodium acetate, sodium citrate, and the like. In some embodiments, the salt is sodium chloride, ammonium chloride, sodium citrate, or a combination thereof.

When present, a representative amount of salt is about 0.5% by weight or more, about 1.0% by weight or more, or about 1.5% by weight or more, but will typically make up about 10% or less of the total weight of the effervescent composition, or about 7.5% or less, or about 5% or less (e.g., from about 0.5 to about 5% by weight). In specific embodiments, the effervescent composition comprises sodium citrate in an amount by weight of from about 2 to about 3%, and sodium chloride in an amount by weight of from about 0.1 to about 0.5%, based on the total weight of the effervescent composition.

Binders

A binder (or combination of binders) may be employed in certain embodiments. Typical binders can be organic or inorganic, or a combination thereof. Representative binders include cellulose derivatives, povidone, sodium alginate, starch-based binders, pectin, carrageenan, pullulan, zein, and the like, and combinations thereof. A binder may be employed in amounts sufficient to provide the desired physical attributes and physical integrity to the effervescent composition. The amount of binder utilized in the effervescent composition can vary based on the binder and the desired effervescent composition properties, but when present, it is typically up to about 30% by weight, and certain embodiments are characterized by a binder content of at least about 0.1% by weight, such as about 0.5 to about 30% by weight, or about 1 to about 10% by weight, based on the total weight of the effervescent composition.

Suitable binders include cellulose derivatives, such as cellulose ethers (including carboxyalkyl ethers), meaning cellulose polymers with the hydrogen of one or more hydroxyl groups in the cellulose structure replaced with an alkyl, hydroxyalkyl, or aryl group. Non-limiting examples of such cellulose derivatives include methylcellulose, hydroxypropylcellulose ("HPC"), hydroxypropylmethylcellulose ("HPMC"), hydroxyethyl cellulose, and carboxymethylcellulose ("CMC").

Other suitable binders include a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. When present, natural gum binder materials are typically present in an amount of up to about 5% by weight, for example, from about 0.1, about 0.2, about 0.3, about 0.4, about 0.5, about 0.6, about 0.7, about 0.8, about 0.9, or about 1%, to about 2, about 3, about 4, or about 5% by weight, based on the total weight of the effervescent composition.

Buffering Agents

In certain embodiments, the effervescent composition of the present disclosure can comprise pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. Non-limiting examples of suitable buffers include alkali metals acetates, glycinates, phosphates, glycerophosphates, citrates, carbonates, hydrogen carbonates, borates, or mixtures thereof.

Where present, the buffering agent is typically present in an amount less than about 5% by weight, based on the weight of the effervescent composition, for example, from about 0.1% to about 5%, such as, e.g., from about 0.1% to about 1%, or from about 0.1% to about 0.5% by weight, based on the total weight of the effervescent composition.

Colorants

A colorant may be employed in amounts sufficient to provide the desired physical attributes to the effervescent composition. Examples of colorants include various dyes and pigments, such as caramel coloring and titanium dioxide. The amount of colorant utilized in the effervescent composition can vary, but when present is typically up to about 3% by weight, such as from about 0.1%, about 0.5%, or about 1%, to about 3% by weight, based on the total weight of the effervescent composition.

Humectants

In certain embodiments, one or more humectants may be employed in the effervescent composition. Examples of humectants include, but are not limited to, glycerin, propylene glycol, and the like. Where included, the humectant is typically provided in an amount sufficient to provide desired moisture attributes to the effervescent composition. Further, in some instances, the humectant may impart desirable flow characteristics to the effervescent composition for depositing in a mold.

When present, a humectant will typically make up about 5% or less of the weight of the effervescent composition (e.g., from about 0.1 to about 5% by weight), for example, from about 0.1% to about 1% by weight, or about 1% to about 5% by weight, based on the total weight of the effervescent composition.

Tobacco Material

In some embodiments, the effervescent composition may include a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia,* and *N. spegazzinii*. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al., U.S. Pat. No. 7,025,066 to Lawson et al.; U.S. Pat. No. 7,798,153 to Lawrence, Jr. and U.S. Pat. No. 8,186,360 to Marshall et al.; each of which is incorporated herein by reference. Descriptions of various types of tobaccos, growing practices and harvesting practices are set forth in *Tobacco Production, Chemistry and Technology*, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

The *Nicotiana* species can, in some embodiments, be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be included within an effervescent composition as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment. In some embodiments, the tobacco material comprises tobacco leaf (lamina). The effervescent composition disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina).

In certain embodiments, the tobacco material comprises solid tobacco material selected from the group consisting of lamina and stems. The tobacco that is used for the mixture most preferably includes tobacco lamina, or a tobacco lamina and stem mixture (of which at least a portion is smoke-treated). Portions of the tobaccos within the mixture may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the d mixture optionally may incorporate tobacco that has been fermented. See, also, the types of tobacco processing techniques set forth in PCT WO2005/063060 to Atchley et al., which is incorporated herein by reference.

The tobacco material is typically used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like. Most preferably, the plant material is relatively dry in form during grinding or milling, using equipment such as hammer mills, cutter heads, air control mills, or the like. For example, tobacco parts or pieces may be ground or milled when the moisture content thereof is less than about 15% by weight, or less than about % by weight. Most preferably, the tobacco material is employed in the form of parts or pieces that have an average particle size between 1.4 millimeters and 250 microns. In some instances, the tobacco particles may be sized to pass through a screen mesh to obtain the particle size range required. If desired, air classification equipment may be used to ensure that small sized tobacco particles of the desired sizes, or range of sizes, may be collected. If desired, differently sized pieces of granulated tobacco may be mixed together.

The manner by which the tobacco is provided in a finely divided or powder type of form may vary. Preferably, tobacco parts or pieces are comminuted, ground or pulverized into a powder type of form using equipment and techniques for grinding, milling, or the like. Most preferably, the tobacco is relatively dry in form during grinding or milling, using equipment such as hammer mills, cutter heads, air control mills, or the like. For example, tobacco parts or pieces may be ground or milled when the moisture content thereof is less than about 15% by weight to less than about 5% by weight. For example, the tobacco plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25% by weight, often less than about 20%, and frequently less than about 15% by weight.

For the preparation of tobacco-containing effervescent compositions, it is typical for a harvested plant of the *Nicotiana* species to be subjected to a curing process. The tobacco materials incorporated within the effervescent composition as disclosed herein are those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int.*, 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.*, 21, 305-320 (2005) and Staaf et al., *Beitrage Tabakforsch. Int.*, 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos and various blends of any of the foregoing tobaccos.

The tobacco material may also have a so-called "blended" form. For example, the tobacco material may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other example tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other example tobacco blends incorporate about 20 to about 30 parts Oriental tobacco and about 70 to about 80 parts flue-cured tobacco on a dry weight basis.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in U.S. Pat. Nos. 8,434,496, 8,944,072, and 8,991,403 to Chen et al., which are all incorporated herein by reference. In certain embodiments, this type of treatment is useful where the original tobacco material is subjected to heat in the processes previously described.

In various embodiments, the tobacco material can be treated to extract a soluble component of the tobacco material therefrom. "Tobacco extract" as used herein refers to the isolated components of a tobacco material that are extracted from solid tobacco pulp by a solvent that is brought into contact with the tobacco material in an extraction process. Various extraction techniques of tobacco materials can be used to provide a tobacco extract and tobacco solid material. See, for example, the extraction processes described in US Pat. Appl. Pub. No. 2011/0247640 to Beeson et al., which is incorporated herein by reference. Other example techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein.

In some embodiments, the type of tobacco material is selected such that it is initially visually lighter in color than other tobacco materials to some degree (e.g., whitened or bleached). Tobacco pulp can be whitened in certain embodiments according to any means known in the art, and as described above in reference to color-eliminated active ingredients.

Typical inclusion ranges for tobacco materials can vary depending on the nature and type of the tobacco material, and the intended effect on the final effervescent composition, with an example range of up to about 30% by weight (or up to about 20% by weight or up to about 10% by weight or up to about 5% by weight), based on total weight of the effervescent composition (e.g., about 0.1 to about 15% by weight). In some embodiments, the products of the disclosure can be characterized as completely free or substantially free of tobacco material (other than purified nicotine as an active ingredient). For example, certain embodiments can be characterized as having less than 1% by weight, or less than 0.5% by weight, or less than 0.1% by weight of tobacco material, or 0% by weight of tobacco material.

Oral Care Additives

In some embodiments, the effervescent composition comprises an oral care ingredient (or mixture of such ingredients). Oral care ingredients provide the ability to inhibit tooth decay or loss, inhibit gum disease, relieve mouth pain, whiten teeth, or otherwise inhibit tooth staining, elicit salivary stimulation, inhibit breath malodor, freshen breath, or the like. For example, effective amounts of ingredients such as thyme oil, eucalyptus oil and zinc (e.g., such as the ingredients of formulations commercially available as ZYTEX® from Discus Dental) can be incorporated into the effervescent composition. Other examples of ingredients that can be incorporated in desired effective amounts within the present effervescent composition can include those that are incorporated within the types of oral care compositions set forth in Takahashi et al., Oral Microbiology and Immunology, 19(1), 61-64 (2004); U.S. Pat. No. 6,083,527 to Thistle; and US Pat. Appl. Pub. Nos. 2006/0210488 to Jakubowski and 2006/02228308 to Cummins et al. Other exemplary ingredients of tobacco containing-formulation include those contained in formulations marketed as MALTISORB® by Roquette and DENTIZYME® by NatraRx. When present, a representative amount of oral care additive is at least about 1%, often at least about 3%, and frequently at least about 5% of the total dry weight of the effervescent composition. The amount of oral care additive within the effervescent composition will not typically exceed about 30%, often will not exceed about 25%, and frequently will not exceed about 20%, of the total dry weight of the effervescent composition.

Processing Aids

If necessary for downstream processing of the effervescent composition, such as granulation, mixing, or molding, a flow aid can also be added to the effervescent composition in order to enhance flowability of the effervescent composition. Exemplary flow aids include microcrystalline cellulose, silica, polyethylene glycol, stearic acid, calcium stearate, magnesium stearate, zinc stearate, sodium stearyl fumarate, carnauba wax, and combinations thereof. In some embodiments, the flow aid is silica, stearic acid, magnesium stearate, or a combination thereof. In some embodiments, the flow aid is sodium stearyl fumarate.

When present, a representative amount of flow aid may make up at least about 0.5 percent or at least about 1 percent, of the total dry weight of the effervescent composition. Preferably, the amount of flow aid within the effervescent composition will not exceed about 5 percent, and frequently will not exceed about 3 percent, of the total dry weight of the effervescent composition.

Emulsifier

In certain embodiments, an emulsifier may be added. In certain embodiments, lecithin can be added to the effervescent composition to provide smoother textural properties of the effervescent composition and to improve flowability and mixing of the lipid with the remaining components of the effervescent composition. Lecithin can be used in an amount of about 0.01 to about 5% by dry weight of the effervescent composition, such as about 0.1 to about 2.5% or about 0.1 to about 1.0%.

Other Additives

Other additives can be included in the disclosed effervescent composition. For example, the effervescent composition can be processed, blended, formulated, combined, and/or mixed with other materials or ingredients. The additives can be artificial, or can be obtained or derived from herbal or biological sources. Examples of further types of additives include thickening or gelling agents (e.g., fish gelatin), emulsifiers, preservatives (e.g., potassium sorbate and the like), disintegration aids, or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., US Pat. App. Pub. No. 2010/0291245 to Gao et al., and US Pat. App. Pub. No. 2007/0062549 to Holton, Jr. et al., each of which is incorporated herein by reference. In some embodiments, the effervescent composition includes an emulsifier. In some embodiments, the emulsifier is lecithin.

Typical inclusion ranges for such additional additives can vary depending on the nature and function of the additive and the intended effect on the final effervescent composition, with an example range of up to about 10% by weight, based on total weight of the effervescent composition (e.g., about 0.1 to about 5% by weight).

The aforementioned additives can be employed together (e.g., as additive formulations) or separately (e.g., individual additive components can be added at different stages involved in the preparation of the final effervescent composition). Furthermore, the aforementioned types of additives may be encapsulated as provided in the final product or effervescent composition. Example encapsulated additives are described, for example, in WO2010/132444 to Atchley, which has been previously incorporated by reference herein.

Adapted for Oral Use

Provided herein is an effervescent composition adapted for oral use. The term "adapted for oral use" as used herein means that the effervescent composition is provided in a form such that during use, saliva in the mouth of the user causes the effervescent material to effervesce in the oral cavity, and saliva in the mouth of the user causes one or more of the components of the effervescent composition (e.g., flavoring agents and/or active ingredients) to pass into the mouth of the user. In certain embodiments, the effervescent composition is adapted to deliver components to a user through mucous membranes in the user's mouth, the user's digestive system, or both, and, in some instances, said component is an active ingredient (including, but not limited to, for example, a stimulant) that can be absorbed through the mucous membranes in the mouth or absorbed through the digestive tract when the effervescent composition is used.

Effervescent compositions adapted for oral use as described herein may take various forms, including gels, pastilles, gums, lozenges, tablets, powders, and pouches. Gels can be soft or hard. Certain products configured for oral use are in the form of pastilles. As used herein, the term "pastille" refers to a dissolvable oral product made by solidifying a liquid or gel composition so that the final product is a somewhat hardened solid gel. The rigidity of the gel is highly variable. Certain effervescent compositions of the disclosure are in the form of solids, which may be meltable. Certain effervescent compositions can exhibit, for example, one or more of the following characteristics: crispy, granular, chewy, syrupy, pasty, fluffy, smooth, and/or creamy. In certain embodiments, the desired textural property can be selected from the group consisting of adhesiveness, cohesiveness, density, dryness, fracturability, graininess, gumminess, hardness, heaviness, moisture absorption, moisture release, mouthcoating, roughness, slipperiness, smoothness, viscosity, wetness, and combinations thereof.

The hardness of the effervescent composition of the disclosure can vary, but is typically at least about 5 kp (kiloponds), such as at least about 8 kp, at least about 10 kp, or at least about 12 kp (e.g., a hardness range of about 5 kp to about 20 kp or about 8 kp to about 15 kp). Hardness can be measured using a hardness tester such as a Varian VK 200 or equivalent.

The effervescent composition can be formed into a variety of shapes, including pills, tablets, spheres, strips, films, sheets, coins, cubes, beads, ovoids, obloids, cylinders, bean-shaped, sticks, or rods. Cross-sectional shapes of the effervescent composition can vary, and example cross-sectional shapes include circles, squares, ovals, rectangles, and the like. Such shapes can be formed in a variety of manners using equipment such as moving belts, nips, extruders, granulation devices, compaction devices, and the like.

In certain embodiments, the effervescent composition is in the form of an edible film (as described in Example 15). One or more components of the effervescent composition (effervescent material, sweetener, salt, active ingredient, and the like) may be present of the surface and/or within the body of the film. In some embodiments, the film contains lower molecular weight polymers and/or other polymers such as hydroxypropylmethylcellulose, carboxymethylcellulose, pullulan, alginates, humectants, or combinations thereof. Other materials such as microcrystalline cellulose may be added to the film.

In certain embodiments, the effervescent composition is in the form of a compressed or molded pellet. Example pellet weights range from about 250 mg to about 1500 mg, such as about 250 mg to about 700 mg, or from about 700 mg to about 1500 mg. The pellet can have any of a variety of shapes, including traditional pill or tablet shapes. Certain embodiments of the disclosure will be described with reference to FIGS. 1A, 1B, and 1C, in which non-limiting examples of possible pellet shapes are provided. Referring to FIG. 1A, there is shown in a perspective view an embodiment of a pellet comprising the effervescent composition in the form of a tablet, the tablet having a diameter and a thickness. Referring to FIG. 1B, there is shown in a perspective view an embodiment of a pellet comprising the effervescent composition in a tablet having an ovoid shape, the tablet having a length, a width, and a thickness. Referring to FIG. 1C, there is shown in a perspective view an embodiment of a pellet comprising the effervescent composition in a tablet having the shape of a sphere, the sphere having a diameter.

The precise shape and size of such pellets is immaterial, but generally, a pellet will have a length, width, and thickness, or a diameter and thickness, which provide a relatively large surface area. The dimensions will vary based on the weight of the pellet. Example pellet sizes include pellets having a length and width in the range of about 3 mm to about 20 mm, and more typically from about 5 to about 18 mm. Example pellet sizes include pellets having a thickness in the range of about 3 to about 10 mm.

In some embodiments, the pellet has a length of from about 15 mm to about 20 mm, a width of from about 6 to about 10 mm, and a thickness of from about 3 to about 6 mm. In a particular embodiment, the length is about 18 mm, the width is about 9 mm, and the thickness is about 5 mm. In some embodiments, the pellet has a diameter of from about 9 mm to about 20 mm, and a thickness of from about 3 to about 10 mm, or from about 4 to about 6 mm.

In some embodiments, the effervescent composition is in the form of a pellet of ovoid or obloid shape having a length and width, each of which is greater than the thickness. Such embodiments may be described in terms of an aspect ratio, defined herein as the ratio of the smallest dimension to the largest dimension. In some embodiments, the effervescent composition is in the form of a tablet having an aspect ratio of from about 1.5 to about 3. In certain embodiments, it may be advantageous to select parameters such as aspect ratio, and the associated thickness, width, length, or diameter, to provide a product having a high surface area. Without wishing to be bound by theory, it is believed that high surface area products, by exposing more surface area to moisture (e.g., the saliva present in the mouth of the consumer), allow for a favorable rate of effervescence, which may result in a positive consumer experience.

The effervescent composition of the present disclosure may be dissolvable or meltable. As used herein, the terms "dissolve," "dissolving," "dissolvable" and "meltable" are used interchangeably, and refer to effervescent compositions having aqueous-soluble components that interact with moisture in the oral cavity and enter into solution, thereby causing gradual consumption of the product. According to one aspect, the dissolvable product is capable of lasting in the user's mouth for a given period of time until it completely dissolves. Dissolution rates can vary over a wide range, from about 1 minute or less to about 60 minutes. For example, fast release effervescent compositions typically dissolve and/or release the active substance in about 2 minutes or less, often about 1 minute or less (e.g., about 50 seconds or less, about 40 seconds or less, about 30 seconds or less, or about 20 seconds or less). Dissolution can occur by any means, such as melting, mechanical disruption (e.g., chewing), enzymatic or other chemical degradation, or by disruption of the interaction between the components of the effervescent composition. In some embodiments, the product can be meltable as described herein above, and discussed, for example, in US Patent App. Pub. No. 2012/0037175 to Cantrell et al. In other embodiments, the products do not dissolve during the product's residence in the user's mouth.

In one embodiment, the effervescent composition of the present disclosure is disposed within a moisture-permeable container (e.g., a water-permeable pouch) as described in Examples 11-15. Such effervescent compositions in the water-permeable pouch format are typically used by placing one pouch containing the effervescent composition in the mouth of a human subject/user. Generally, the pouch is placed somewhere in the oral cavity of the user, for example under the lips, in the same way as moist snuff products are generally used. The pouch preferably is not chewed or swallowed. Exposure to saliva then causes some of the components of the effervescent composition therein (e.g., flavoring agents and/or active ingredients) to pass through e.g., the water-permeable pouch and provide the user with flavor and satisfaction, and the user is not required to spit out any portion of the effervescent composition. After about 10 minutes to about 60 minutes, typically about 15 minutes to about 45 minutes, of use/enjoyment, substantial amounts of the effervescent composition have been absorbed through oral mucosa of the human subject, and the pouch may be removed from the mouth of the human subject for disposal.

Accordingly, in certain embodiments, the effervescent composition as disclosed herein and any other components noted above are combined within a moisture-permeable packet or pouch that acts as a container for use of the effervescent composition to provide a pouched product configured for oral use. Certain embodiments of the disclosure will be described with reference to FIG. 2, and these described embodiments involve snus-type products having an outer pouch and containing an effervescent composition as described herein. As explained in greater detail below, such embodiments are provided by way of example only, and the pouched products of the present disclosure can include the effervescent composition in other forms. The composition/construction of such packets or pouches, such as the container pouch 102 in the embodiment illustrated in FIG. 2, may be varied. Referring to FIG. 2, there is shown a first embodiment of a pouched product 100. The pouched product 100 includes a moisture-permeable container in the form of a pouch 102, which contains a material 104 comprising an effervescent composition as described herein.

A suitable fleece, for example, may be formed of a plurality of fibers. The term "fiber" as used herein includes both fibers of finite length, such as conventional staple fibers and nanofibers, as well as substantially continuous structures, such as continuous filaments, unless otherwise indicated. The fibers can have a substantially round or circular cross section or non-circular cross sections (for example, oval, rectangular, multi-lobed, and the like). The fibers can be provided in a variety of configurations, and the fibers particularly can include multicomponent fibers.

In some embodiments, the fleece can be in the form of a non-woven material. The term "nonwoven" is used herein in reference to fibrous materials, webs, mats, batts, or sheets in which fibers are aligned in an undefined or random orientation. In some embodiments, the plurality of fibers used in forming a fleece may include heat sealable and/or meltable binder fibers.

Suitable packets, pouches or containers of the type used for the manufacture of smokeless tobacco products are available under the tradenames CatchDry, Ettan, General, Granit, Goteborgs Rape, Grovsnus White, Metropol Kaktus, Mocca Anis, Mocca Mint, Mocca Wintergreen, Kicks, Probe, Prince, Skruf and TreAnkrare. The effervescent composition may be contained in pouches and packaged, in a manner and using the types of components used for the manufacture of conventional snus types of products. The pouch provides a liquid-permeable container of a type that may be considered to be similar in character to the mesh-like type of material that is used for the construction of a tea bag. Components of the effervescent composition readily diffuse through the pouch and into the mouth of the user.

Non-limiting examples of suitable types of pouches are set forth in, for example, U.S. Pat. No. 5,167,244 to Kjerstad and U.S. Pat. No. 8,931,493 to Sebastian et al.; as well as US Patent App. Pub. Nos. 2016/0000140 to Sebastian et al.; 2016/0073689 to Sebastian et al.; 2016/0157515 to Chapman et al.; and 2016/0192703 to Sebastian et al., each of which is incorporated herein by reference. Pouches can be provided as individual pouches, or a plurality of pouches (e.g., 2, 4, 5, 10, 12, 15, 20, 25 or 30 pouches) can be connected or linked together (e.g., in an end-to-end manner) such that a single pouch or individual portion can be readily removed for use from a one-piece strand or matrix of pouches.

An example pouch may be manufactured from materials, and in such a manner, such that during use by the user, the pouch undergoes a controlled dispersion or dissolution. Such pouch materials may have the form of a mesh, screen, perforated paper, permeable fabric, or the like. For example, pouch material manufactured from a mesh-like form of rice paper, or perforated rice paper, may dissolve in the mouth of the user. As a result, the pouch and effervescent composition each may undergo complete dispersion within the mouth of the user during normal conditions of use, and hence the pouch and effervescent composition both may be ingested by the user. Other examples of pouch materials may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the effervescent composition contents permeate through the pouch material prior to the time that the pouch undergoes loss of its physical integrity. If desired, flavoring ingredients, disintegration aids, and other desired components, may be incorporated within, or applied to, the pouch material. In some embodiments, a portion of the effervescent material, or a component thereof, may be dispersed within or on the pouch material. For example, in some embodiments, the pouch comprises a fleece material, and the fleece material has at least a portion of the acid component, the base component, or both coated/disposed thereon or impregnated therein. In some embodiments, the pouch fleece material may be coated with one or more effervescent components. For example, the fleece may be coated with encapsulated bicarbonate and/or encapsulated acid component. The particles of components of the composition (e.g., effervescent materials) may be adhered to the fleece material using an adhesive, polymer agent, and/or a melted material such as an oil.

The amount of material contained within each product unit, for example, a pouch, may vary. In some embodiments, the weight of the effervescent composition within each pouch is at least about 50 mg, for example, from about 50 mg to about 1500 mg, such as from about 100 to 800 about mg, or from about 700 to about 1500 mg. If desired, other components can be contained within each pouch. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and U.S. Pat. No. 6,923,981 to Leung et al.; and The EFSA Journal (2004) 85, 1-32; which are incorporated herein by reference.

In certain embodiments, one or more active ingredients as described herein are included in the effervescent composition within the pouched product, and optionally, one or more further active ingredients are disposed in or on the external surface of the product (e.g., on or in the pouch material as disclosed herein). The effervescent components may be incorporated in the structure of the fleece material. In some embodiments, separate location of the active ingredients may allow differential release profiles (e.g., one active ingredient may be rapidly available to the mouth and/or digestive system, and the other active ingredient may be released more gradually with product use).

A pouched product as described herein can be packaged within any suitable inner packaging material and/or outer container. See also, for example, the various types of containers for smokeless types of products that are set forth in U.S. Pat. No. 7,014,039 to Henson et al.; U.S. Pat. No. 7,537,110 to Kutsch et al.; U.S. Pat. No. 7,584,843 to Kutsch et al.; U.S. Pat. No. 8,397,945 to Gelardi et al., D592,956 to Thiellier; D594,154 to Patel et al.; and D625,178 to Bailey et al.; US Pat. Pub. Nos. 2008/0173317 to Robinson et al.; 2009/0014343 to Clark et al.; 2009/0014450 to Bjorkholm; 2009/0250360 to Bellamah et al.; 2009/0266837 to Gelardi et al.; 2009/0223989 to Gelardi; 2009/0230003 to Thiellier; 2010/0084424 to Gelardi; and 2010/0133140 to Bailey et al; 2010/0264157 to Bailey et al.; and 2011/0168712 to Bailey et al. which are incorporated herein by reference.

Preparation of the Effervescent Composition

The manner by which the various components of the effervescent compositions (e.g., effervescent material, filler, active ingredient, flavoring agent, and optionally, a lipid) are combined may vary. As such, the overall effervescent composition with e.g., powdered composition components may be relatively uniform in nature. The components noted above, which may be in liquid or dry solid form, can be admixed in a pretreatment step prior to mixture with any remaining components of the composition, or simply mixed together with all other liquid or dry ingredients.

The effervescent compositions of the disclosure are prepared, for example, by dry-blending dry ingredients, such as filler, sweeteners, salts, and the like. In certain embodiments, water can be added to the dry blend at this stage. Additionally, it is optional to add, such as by spraying, active ingredients and/or flavoring agents to the dry blend, followed by mixing.

For preparation of meltable effervescent compositions, (as described in Examples 5-10), the lipid is typically heated to slightly above the melting temperature such that the lipid is liquefied. Optionally, active ingredients, flavoring agents, and/or lecithin can be added to the liquefied lipid at this stage. Thereafter, all or a portion of the liquefied lipid can be blended with the dry blend and mixed until the effervescent composition reaches the desired level of homogeneity or until the desired textural properties are achieved. The effervescent composition can be divided into discrete portions, such as by pouring the effervescent composition into a sheet-like structure, cooling, and then cutting the structure into individual portions, or by depositing the effervescent composition into molds and allowing to cool. The melt may be coated, with, for example, processing aids such oils, hard coatings, flavoring agents, and/or active agents as disclosed herein. Alternatively, or in addition, the melt may be coated with the effervescent mixture or a component thereof as disclosed herein, for example, the acid agent while the bicarbonate is present in the body of the melt, or the bicarbonate while the acid is present in the body of the melt.

The various components of the effervescent composition may be contacted, combined, or mixed together using any mixing technique or equipment known in the art. Any mixing method that brings the effervescent composition ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference. In some embodiments, the components forming the effervescent composition are prepared such that the mixture thereof may be used in a starch molding process for forming the effervescent composition. Manners and methods for formulating effervescent compositions will be apparent to those skilled in the art. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

In some embodiments, the effervescent composition is in the form of a pellet or tablet (as described in Examples 1-4). Compressed effervescent composition pellets can be produced by compacting the effervescent composition, including any associated formulation components, in the form of a pellet, and optionally coating each pellet with an overcoat material. Example granulation devices are available as the FL-M Series granulator equipment (e.g., FL-M-3) from Vector Corporation and as WP 120V and WP 200VN from Alexanderwerk, Inc. Example compaction devices, such as compaction presses, are available as Colton 2216 and Colton 2247 from Vector Corporation and as 1200i, 2200i, 3200, 2090, 3090 and 4090 from Fette Compacting. Devices for providing outer coating layers to compacted pelletized compositions are available as CompuLab 24, CompuLab 36, Accela-Cota 48 and Accela-Cota 60 from Thomas Engineering.

In one embodiment, the process for making the pellet or tablet involves first forming a granulation mixture, which may be tobacco-containing, granulating the mixture, optionally adding a binder, or a solution thereof, to produce an intermediate granular product, and then blending the granules with a second composition comprising the additional effervescent composition components to form the final effervescent composition. The final effervescent composition is then compressed into pellet or tablet form and optionally coated. The granulation mixture typically includes a first portion of the acid component of the effervescent material (e.g., a first portion of a mixture of citric acid and tartaric acid), optionally a first portion of the base component of the effervescent material (e.g., a carbonate material), and optionally one or more binders, fillers, lipids, sweeteners, flavorants, active ingredients, colorants, compressibility aids, or other additives. It is desirable to maintain the effervescent composition in a relatively inert state during manufacture so that the effervescing effect is preserved in the final product. Bicarbonate base materials are more reactive with an acid to create effervescence in the presence of moisture and therefore can lead to premature reactivity in the product. The granulation mixture is typically relatively dry, meaning no liquid ingredients are introduced and instead the mixture contains essentially all dry powder ingredients. The granulation material may be mixed with a binder solution (e.g., by spraying the binder solution into the granulator) and granulated to a desired particle size, such as about 100 to about 200 microns. As would be understood in the art, the binder solution facilitates agglomeration of the dry powder granulation mixture into larger granules.

The binder solution used in the granulation process can be any aqueous or alcohol-based solution containing a binding agent, particularly a polymeric binding agent such as povidone or hydroxypropylcellulose, and can contain other additives including any of the additives discussed herein such as mannitol, maltodextrin, tobacco material, sweeteners, flavorants, and effervescent materials. The binder solution will typically have a solids content of about 5 to about 20 percent (w/w), and preferred solvents include water and ethanol. The binder solution used in the granulation process can be aqueous in nature without causing significant premature effervescence within the granulation mixture.

Following granulation, the granules are advantageously dried, typically to a moisture level of less than about 7.0 weight percent, more typically less than about 6.5 weight percent, and often less than about 6.0 weight percent (e.g., a range of about 4.0 to about 7.0 weight percent). An exemplary moisture level is about 5.5 weight percent.

The dried granules are then blended with the remaining desired components of the effervescent composition, including for example, a second portion of the acid component of the effervescent material (e.g., a second portion of a mixture of citric acid and tartaric acid), a base component of the effervescent material (e.g., a bicarbonate material), and optionally one or more binders, fillers, lipids, sweeteners, flavorants, colorants, flow aids, or other additives. The blending of the granulated material with the remaining ingredients can be accomplished using a granulator or any other mixing device. The final blended material may then be compressed using conventional tableting techniques.

In another aspect, the disclosure provides pellets formed using a rotor granulator wherein dry powder layers are accumulated on a substantially spherical core material to form roughly spherical pellet products. The core material can vary, but typically comprises a compressible powder material such as microcrystalline cellulose, sugar, or salt. The core material can also incorporate tobacco material if desired. In some embodiments, the core material may comprise a lipid. The diameter of the core material is typically between about 600 microns and about 3,000 microns. Large core sizes can be advantageous because layering efficiency increases with increases in core size. Commercially available microcrystalline cellulose having a size in the range of about 700 to about 900 microns is one exemplary core material. In another example, an extruded tobacco product in the size range of about 2 to about 3 mm is used as the core material. The extruded tobacco product can be a product similar to the commercially available CAMEL Orbs product by R. J. Reynolds Tobacco Company.

The core material is charged to a rotor granulator, such as GXR-35 GRANUREX® Rotor Processor available from Vector Corporation, and a desired powder coating material and accompanying binder solution can be applied to the core material, thereby building up additional layers on the core and increasing the size of the spherical pellet. The powder coating material will typically include a filler as the predominate ingredient, along with other dry powder components including any of the additives noted herein such as salts, active ingredients, flavorants, sweeteners, lipid, binders, buffering agents, colorants, humectants, oral care additives, preservatives, syrups, disintegration aids, antioxidants, additives derived from an herbal or botanical source, flow aids, compressibility aids, and combinations thereof. The particle size of the powder material used in the rotor granulation process can vary, but efficiency of the layering process increases with decreasing particle size.

Example binder solutions for the rotor granulation process include aqueous or alcohol-based solutions of polymer binding agents including povidone and hydroxypropylcellulose, and can contain other additives including any of the additives discussed herein such as mannitol, maltodextrin, tobacco material, sweeteners, flavorants, and effervescent materials. The binder solution will typically have a solids content of about 5 to about 20 percent (w/w), and preferred solvents include water and ethanol. Ethanol or other alcohol solvents are advantageous in some embodiments because the use of non-aqueous solvents can reduce the moisture level in the pellet, which can reduce the drying time required to prepare the final product.

In the context of effervescent products of the type described herein, rotor granulation allows the user to build a layered product where only certain predetermined layers include the effervescent material. For example, a multi-layer product might contain one or more layers of non-effervescent composition and one or more layers of a composition containing the effervescent material, where the two types of layers are present in any desired order. The product may include a core surrounded by a non-effervescent layer followed by an outer layer containing an effervescent material. The core may comprise a portion or all of the optional lipid. In addition, the production process could successively build concentric effervescent and non-effervescent layers repeatedly until the desired product size is reached. In this manner, a multi-layer product having a unique sensory profile can be created where effervescence occurs multiple times during use as outer layers dissolve in the oral cavity and expose additional effervescent material. The number of layers can vary, but rotor granulation products typically include a core surrounded by 1 to about 20 layers, more often about 2 to about 10 layers.

In one embodiment of a rotor granulation process, a non-effervescent powder coating material is prepared comprising one or more components, such as fillers, binders, flavorants, or the like. An effervescent powder coating material is also prepared comprising an effervescent material as disclosed herein, and one or more components, such as one or more fillers, tobacco material, flavorants, sweeteners, or other components of the effervescent composition as disclosed herein.

The effervescent and non-effervescent layers are concentrically layered in any order on a core material using a rotor granulation process and coating materials such as those described in US Pat. Pub. No. 2010/0170522 to Sun et al., which is incorporated by reference herein. For example, the core material can have a first layer of the non-effervescent material followed by an overlying layer of the effervescent material. If desired, a barrier layer (e.g., a layer consisting solely of binder solution) can be sprayed on the pellet between each effervescent and non-effervescent layer and dried in order to reduce interaction between the effervescent material and moisture that may be present in the non-effervescent layers.

Other methods of preparing multi-layered products could also be used. For example, a conventional tablet press could be used to manufacture a layered product by simply adding multiple distinct granular compositions to the tablet press. In one embodiment, a multi-layer tablet or pellet is formed by adding a granular mixture comprising a first composition to the tablet press mold followed by addition of a granular mixture containing a second composition different from the first, either or both of which may be effervescent. This process could be repeated until the desired number of layers is reached. Thereafter, applying pressure to the tablet press mold will result in a pellet or tablet product with multiple, distinct layers. Multi-layered products made using this process could possess the same characteristics as described above in connection with rotor granulation systems. For instance, the pressed pellet could contain multiple effervescent and non-effervescent layers. Referring to FIG. 3A, there is shown in a perspective view a non-limiting embodiment of a tablet having two layers; a top layer and a bottom layer, in which at least one of the layers comprises the effervescent composition.

In yet another embodiment, a layered product could be created using a "pellet-in-pellet" approach where a first pellet containing a first composition is compressed and formed using a tablet press and then modified by addition of distinct outer layers. The outer layers can be added by introducing a granular mixture of desired composition into the tablet press mold on each side of a pre-formed pellet that is also introduced to the mold. The tablet press can be used to compress the granular mixtures onto the pre-formed pellet to create a layered structure. Referring to FIG. 3B, there is shown in a perspective view a non-limiting embodiment of a tablet having an inner layer and an outer layer, in which at least one of the layers comprises the effervescent composition. Referring to FIG. 3C, there is shown in a perspective view a non-limiting embodiment of a tablet having a spherical shape comprising an inner layer and an outer layer, in which at least one of the layers comprises the effervescent composition.

The effervescent composition can include an optional outer coating, which can help to improve storage stability of the product as well as improve the packaging process by reducing friability and dusting. The coating typically comprises a film-forming polymer, such as a cellulosic polymer, an optional plasticizer, and optional flavorants, colorants, salts, sweeteners or other additives of the types set forth herein. The coating compositions are usually aqueous in nature and can be applied using any pellet or tablet coating technique known in the art, such as pan coating. Example film-forming polymers include cellulosic polymers such as methylcellulose, hydroxypropyl cellulose (HPC), hydroxypropyl methylcellulose (HPMC), hydroxyethyl cellulose, and carboxy methylcellulose. Example plasticizers include aqueous solutions or emulsions of glyceryl monostearate and triethyl citrate.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

EXAMPLES

Aspects of the present invention are more fully illustrated by the following examples, which are set forth to illustrate certain aspects of the present invention and are not to be construed as limiting thereof.

Example 1. Effervescent Tablets Containing Caffeine

Effervescent tablets according to an embodiment of the disclosure were prepared including caffeine as the active ingredient. The dry blend formulation is provided in Table 1. The dry materials (mannitol, maltodextrin, sweetener, caffeine, salt, silicon dioxide, and a pre-formed mixture of sodium bicarbonate, citric acid, and tartaric acid) were each passed through an 18 mesh screen, then mixed in a V-blender until homogenous. Following the mixing period, a punch lubricant (e.g., stearic acid, magnesium stearate, silica/, sodium stearyl fumarate, or combinations thereof) was added as necessary for processing, followed by further mixing. Tablets were prepared using a punch press, forming tablets weighing about 800 mg or about 1000 mg each. The tablets were roughly ovoid in shape, having a length of approximately 18 mm and a width of approximately 9 mm, and with a thickness of approximately 6 mm.

TABLE 1

| Effervescent caffeine tablet ingredients | |
|---|---|
| Dry Ingredients | Weight % |
| mannitol | 25-40 |
| maltodextrin | 25-40 |
| sweetener | 0.1-0.5 |
| caffeine | 1-10 |
| tartaric acid | 4-6 |
| citric acid | 4-6 |
| sodium bicarbonate | 8-15 |
| sodium chloride | 0.1-0.5 |
| silicon dioxide | 0-2 |
| stearic acid | 0-2 |
| magnesium stearate | 0-2 |
| sodium stearyl fumarate | 0-2 |

Example 2. Effervescent Tablet Containing L-Theanine, GABA, and Lemon Balm Extract An effervescent tablet according to an embodiment of the disclosure was prepared according to Example 1, but including a mixture of L-theanine, GABA, and lemon balm extract as the active ingredient. The dry blend formulation is provided in Table 2.

TABLE 2

| Effervescent L-theanine, GABA, and Lemon Balm tablet ingredients | |
|---|---|
| Dry Ingredients | Weight % |
| isomalt | 22-33 |
| Emdex ® | 30-45 |
| sweetener | 0.1-0.5 |
| L-theanine | 3-5 |
| GABA | 4-6 |
| lemon balm extract | 2-8 |
| tartaric acid | 4-6 |
| citric acid | 4-6 |
| sodium bicarbonate | 8-15 |
| sodium chloride | 0.1-0.5 |
| sodium stearyl fumarate | 0.5-1.5 |

Example 3. Effervescent Tablet Containing Caffeine, Taurine, and Vitamin C

An effervescent tablet according to an embodiment of the disclosure was prepared according to Example 1, but including a mixture of caffeine, taurine, and vitamin C as the active ingredient. The dry blend formulation is provided in Table 3.

TABLE 3

| Effervescent caffeine, taurine, and vitamin C tablet ingredients | |
|---|---|
| Dry Ingredients | Weight % |
| isomalt | 20-30 |
| Emdex ® | 30-45 |
| sweetener | 0.1-0.5 |
| caffeine | 3-5 |
| taurine | 4-6 |
| vitamin C | 4-6 |
| sodium citrate | 2-3 |
| tartaric acid | 4-6 |
| citric acid | 4-6 |
| sodium bicarbonate | 8-15 |
| sodium chloride | 0.1-0.5 |
| sodium stearyl fumarate | 0.5-1.5 |

Example 4. Effervescent Tablet Containing Caffeine, L-Theanine, Sunflower Lecithin, and *Panax ginseng*

An effervescent tablet according to an embodiment of the disclosure was prepared according to Example 1, but including a mixture of caffeine, L-theanine, sunflower lecithin, and *Panax ginseng* as the active ingredients. The dry blend formulation is provided in Table 4.

TABLE 4

Effervescent L-theanine, caffeine, sunflower lecithin, and Panax ginseng tablet ingredients

| Dry Ingredients | Weight % |
|---|---|
| isomalt | 22-35 |
| Emdex ® | 28-43 |
| sweetener | 0.1-0.5 |
| caffeine | 3-5 |
| L-theanine | 4-6 |
| sunflower lecithin | 0.5-1.5 |
| Panax ginseng | 0.4-0.6 |
| sodium citrate | 2-3 |
| tartaric acid | 4-6 |
| citric acid | 4-6 |
| sodium bicarbonate | 8-15 |
| sodium chloride | 0.1-0.5 |
| sodium stearyl fumarate | 0.5-1.5 |

Example 5. Effervescent Melt Containing Caffeine

An effervescent melting tablet "melt" according to an embodiment of the disclosure was prepared including caffeine as the active ingredient. The tablet weight was approximately 1500 mg. The batch formulation is provided in Table 5. A 1:1 mixture of tartaric and citric acids was milled to a particle size of less than 180 □m and added to a PVG Super Excel wet grinder, along with powdered sodium chloride (particle size less than 35 □m), isomalt (particle size less than 25 □m), and the remaining dry ingredients. The palm oil was warmed with a hot air gun and added to the grinder, and the combination thoroughly mixed. Tablets were prepared using a punch press, forming tablets weighing about 1500 mg each.

TABLE 5

Melting tablet composition

| Ingredient | Weight % |
|---|---|
| Palm Oil, Paramount B, 95F | 30-50 |
| isomalt | 35-55 |
| citric/tartaric acid mix | 3-6 |
| sodium bicarbonate | 3-6 |
| caffeine | 1-10 |
| sodium chloride | 0.5-1.5 |
| flavorant | 0.1-1 |
| emulsifier | 0.1-1 |
| sweetener | 0.1-1 |

Examples 6-8. Preparation and Evaluation of Effervescent Melts with Small or Large Effervescent Material Particle Sizes Example 6A. Base Melt Composition A base melt composition was prepared by mixing the following ingredients in the indicated weight/total weight percentages: 51.56% Isomalt, 4.69% Paramount X palm oil, 42.19% Paramount C, 1.04% sodium chloride, and 0.42% sunflower lecithin. The base formulation was milled to less than about 15-micron particle size.

Examples 6B and 6C. Powder Acid Blends

A powder acid blend was made by mixing 100.24 g of tartaric acid and 100.26 g of citric acid. The powder mixture was ground and a two fractions were collected as the powder acid blend portion than passed through a 180-micron mesh and was retained on a 53-micron mesh (fraction 6B) and was retained on a 38-micron mesh (fraction 6C).

Examples 6D and 6E. Powder Bicarbonate Blends

Sodium bicarbonate powder was also collected in two fractions: the sodium bicarbonate powder was passed through a 180-micron mesh and was retained on a 53-micron mesh (fraction 6D), and was retained on a 38-micron mesh (fraction 6E).

Example 6F. Dry Effervescent Caffeine Blend—Small Particle

A dry effervescent caffeine blend was prepared by mixing 4.74 g of fraction 6B, 5.77 g of fraction 6D, 0.11 g sucralose, 1.03 g sodium chloride, and 6.04 g of caffeine.

Example 6G. Non-Effervescent Caffeine Melt (Reference)

A reference melt composition was prepared by mixing 95.92 g of the base melt composition of Example 6A, 0.05 g sucralose, 1.00 g sodium chloride, and 3.01 g caffeine. The mixture was heated and deposited in round molds, yielding pieces of about 1.5 g each.

Example 7. Effervescent Melt Containing Caffeine, Large Particles

A large particle effervescent melt containing caffeine was prepared by mixing 85.39 g of the base melt composition of example 6A, 4.77 g of fraction 6B, 5.76 g of fraction 6D, 0.05 g sucralose, 1.02 g sodium chloride, and 3.01 g of caffeine. The mixture was heated and deposited in round molds, yielding pieces of about 1.5 g each.

Example 8. Effervescent Melt Containing Caffeine, Small Particles

A small particle effervescent melt containing caffeine was prepared by mixing 85.77 g of the base melt composition of example 6A, 4.74 g of fraction 6C, 5.71 g of fraction 6E, 0.05 g sucralose, 1.00 g sodium chloride, and 3.01 g caffeine. The mixture was heated and deposited in round molds, yielding pieces of about 1.5 g each.

Results

In an oral sensory evaluation panel, Examples 7 and 8 were found to have a less bitter taste than reference example 6G. Example 8 was found to have greater effervescent action. Without being bound by theory, Example 8 is thought to have an earlier onset of effervescent action due to the smaller particle sizes of the acid mixture and the sodium bicarbonate (fractions 6C and 6E) versus the larger particle sizes of Example 7 (fractions 6B and 6D).

Example 9. Effervescent Coated Melt Containing Caffeine, Small Particle

A coated melt containing caffeine was prepared by mixing 94.82% of the base melt composition of Example 6A, 0.05% sucralose, 0.05% acesulfame-K, 2.00% sodium citrate, and 3.08% caffeine. The mixture was heated and deposited in round molds, yielding pieces of about 1.5 g each. A piece having a weight of 1.36 g was surface coated with 0.023 g of the dry effervescent caffeine blend of Example 6F. The resulting Example 9 gave a rapid initial effervescent action upon oral use of the melt.

Example 10. Palm Oil-Coated Large Particle Size Sodium Bicarbonate Powder

Palm oil-coated large particle sodium bicarbonate was prepared by mixing large particle sodium bicarbonate of fraction 6B with melted Paramount C palm oil. The resulting powder was screened, giving particles that passed through a 250-micron mesh screen. The coated bicarbonate was used in Example 13, below.

Example 11. Pouched Caffeine Dry Mixture (Reference)

A pouched, dry reference example containing caffeine was made as follows: 93.04 g microcrystalline cellulose, 0.05 g sucralose, 1.00 g sodium chloride, and 6.02 g of caffeine were dry blended. About 450 mg of the blend was added to a cellulosic fleece pouch. In an oral sensory evaluation panel, Example 11 was found to have a bitter taste.

Example 12. Pouched Effervescent Caffeine Large Particle Dry Mixture

A pouched, dry effervescent inventive example containing caffeine was made as follows: 82.48 g microcrystalline cellulose, 4.79 g of fraction 6B, 5.79 g of fraction 6D, 0.05 g sucralose, 0.99 g sodium chloride, and 6.03 g of caffeine were dry blended. About 450 mg of the blend was added to a cellulosic fleece pouch. In an oral sensory evaluation panel, Example 12 was found to have effervescence, and a less bitter taste than reference Example 11.

Example 13. Pouched Effervescent Caffeine Dry Mixture, Coated Bicarbonate

A pouched, dry effervescent inventive example containing caffeine was made as follows: 82.89 g microcrystalline cellulose, 4.73 g large particle acid of fraction 6B, 6.99 g palm oil-coated sodium bicarbonate (Example 10), 0.05 g sucralose, 1.06 g sodium chloride, and 6.03 g caffeine were dry blended. About 450 mg of the blend was added to a cellulosic fleece pouch. In an oral sensory evaluation panel, Example 13 was found to have effervescence and a less bitter taste than reference Example 11, and delayed onset of effervescent action relative to Example 12.

Example 14. Dry Effervescent Caffeine Blend—Small Particle

A dry effervescent caffeine blend was prepared by mixing 4.78 g of fraction 6C, 5.79 g of fraction 6E, 0.11 g sucralose, 1.06 g sodium chloride, and 6.04 g of caffeine. This dry effervescent blend was used in Example 15.

Example 15. Edible Film (Inventive)

An edible film effervescent inventive example containing caffeine was made as follows: 52.46 g hydroxypropylmethylcellulose was dissolved in 1500 mL of deionized water. A portion of the resulting mixture (95.31 g) was mixed with 7.81 g of propylene glycol. The mixture was dried in a convection oven at about 60° C. A 4.5 cm diameter circle of the dried mixture, having about 42.62% moisture content, was collected and dusted with the effervescent mixture of Example 14. The effervescent mixture adhered to the surface of the film providing Example 15. Example 15 was found to contain 0.478 g of film material and 0.634 g effervescent mixture. In an oral sensory evaluation panel, Example 15 was found to have effervescence.

What is claimed is:

1. An effervescent composition adapted for oral use, comprising:
    an effervescent material capable of causing effervescence in the oral cavity, wherein the effervescent material has a particle size of less than about 180 microns;
    one or more fillers in a total amount of at least about 30% by weight, based on the total weight of the composition, wherein the one or more fillers includes at least one sugar alcohol, and wherein a particle size of the one or more fillers is less than about 35 microns;
    at least one active ingredient; and
    optionally, a lipid in an amount of at least about 20% by weight.

2. The effervescent composition of claim 1, wherein the effervescent material comprises an acid component and a base component, wherein the base component is a carbonate material, a bicarbonate material, or a mixture thereof.

3. The effervescent composition of claim 2, wherein the acid component is a tricarboxylic acid, a dicarboxylic acid, or a combination thereof.

4. The composition of claim 2, wherein the acid component comprises a combination of a tricarboxylic acid and a dicarboxylic acid in a weight ratio of from about 2:1 to about 1:2.

5. The effervescent composition of claim 2, wherein the acid component is citric acid, tartaric acid, or a combination thereof.

6. The effervescent composition of claim 5, wherein the acid component is a combination of citric acid and tartaric acid in a ratio of from about 2:1 to about 1:2 by weight.

7. The effervescent composition of claim 6, wherein the base component is a bicarbonate material.

8. The effervescent composition of claim 2, wherein the acid component is present in an amount of from about 10% to about 20% by weight, based on the total dry weight of the effervescent composition.

9. The effervescent composition of claim 2, wherein the acid component and the base component are present in about a 1:1 molar ratio.

10. The effervescent composition of claim 1, wherein the effervescent material comprises a sugar material containing an entrapped gaseous component, such that release of the entrapped gaseous component occurs upon dissolution of the sugar material in the oral cavity.

11. The effervescent composition of claim 10, wherein the sugar material containing an entrapped gaseous component is in the form of a gasified sugar material in particulate form, the gasified sugar material particles being in admixture with the one or more fillers and active ingredient.

12. The effervescent composition of claim 1, wherein the at least one active ingredient comprises one or more botanical materials, stimulants, amino acids, vitamins, cannabinoids, cannabimimetics, terpenes, nutraceuticals, pharmaceutical agents, or combinations thereof.

13. The effervescent composition of claim 1, wherein the at least one active ingredient comprises caffeine.

14. The composition of claim 1, comprising:
    from about 10 to about 25 dry weight percent of the effervescent material;

at least about 50 dry weight percent of the one or more fillers;

from about 1 to about 10 dry weight percent of caffeine; and optionally, from about 1 to about 3% dry weight percent of sodium citrate.

15. The effervescent composition of claim 14, wherein the one or more fillers comprise mannitol, maltodextrin, isomalt, polysaccharides, or a combination thereof.

16. The effervescent composition of claim 14, wherein the one or more fillers comprise isomalt, glucose, and starch-derived polysaccharides.

17. The effervescent composition of claim 1, further comprising one or more additives selected from the group consisting of flavorants, sweeteners, taste modifiers, salts, binders, buffering agents, colorants, humectants, oral care additives, preservatives, disintegration aids, antioxidants, flow aids, compressibility aids, and combinations thereof.

18. The effervescent composition of claim 17, wherein a particle size of any flavorants, sweeteners, taste modifiers, salts, binders, buffering agents, colorants, humectants, emulsifiers, oral care additives, preservatives, disintegration aids, antioxidants, flow aids, and compressibility aids which may be present is less than about 35 microns.

19. The effervescent composition of claim 1, wherein the composition is substantially free of tobacco.

20. The effervescent composition of claim 1, wherein the composition is substantially free of nicotine.

21. The effervescent composition of claim 1, wherein the active ingredient comprises a nicotine component.

22. The effervescent composition of claim 1, wherein the composition is a compressed or extruded product having a predetermined shape.

23. The effervescent composition of claim 22, wherein the product is a tablet.

24. The effervescent composition of claim 23, wherein the tablet has an aspect ratio of from about 1.5 to about 3.

25. The effervescent composition of claim 1, wherein the composition is in granular form, and wherein the composition in granular form is enclosed in a pouch to form a pouched product.

26. The effervescent composition of claim 1, wherein the lipid has a melting point of about 29° C. or above.

27. The effervescent composition of claim 1, wherein the lipid has a melting point from about 36° C. to about 45° C.

28. The effervescent composition of claim 1, wherein the lipid is an oil selected from the group consisting of palm oil, palm kernel oil, soybean oil, cottonseed oil, and combinations thereof, wherein the oil may be hydrogenated, partially hydrogenated, or non-hydrogenated.

29. The effervescent composition of claim 1, comprising:
up to about 50 dry weight percent of the lipid;
up to about 20 dry weight percent of the effervescent material;
up to about 50 dry weight percent of the one or more fillers; and
from about 1 to about 10 dry weight percent of caffeine.

30. The effervescent composition of claim 28, wherein the composition is in granular form, and wherein the composition is enclosed in a pouch to form a pouched product.

31. The effervescent composition of claim 29, wherein the pouch comprises a fleece material, and wherein the fleece material has at least a portion of the acid component, the base component, or both disposed thereon or impregnated therein.

32. The effervescent composition of claim 28, in the form of a tablet.

33. The effervescent composition of claim 31, wherein the tablet has an outer surface, and wherein the effervescent material is disposed on said outer surface.

34. The effervescent composition of claim 31, wherein the tablet comprises an inner region comprising the lipid.

35. The effervescent composition of claim 31, wherein the tablet comprises multiple layers comprising:
an effervescent layer comprising the effervescent material; and
at least one non-effervescent layer.

36. The effervescent composition of claim 1, comprising:
isomalt in an amount of from about 22 to about 33% by weight, based on the total weight of the effervescent composition;
a glucose-polysaccharide blend in an amount of from about 30 to about 45% by weight, based on the total weight of the effervescent composition;
a sweetener in an amount of from about 0.1 to about 0.5% by weight, based on the total weight of the effervescent composition;
L-theanine in an amount of from about 3 to about 5% by weight, based on the total weight of the effervescent composition;
gamma-aminobutyric acid in an amount of from about 4 to about 6% by weight, based on the total weight of the effervescent composition;
lemon balm extract in an amount of from about 2 to about 8% by weight, based on the total weight of the effervescent composition;
tartaric acid in an amount of from about 4 to about 6% by weight, based on the total weight of the effervescent composition;
citric acid in an amount of from about 4 to about 6% by weight, based on the total weight of the effervescent composition;
sodium bicarbonate in an amount of from about 8 to about 15% by weight, based on the total weight of the effervescent composition;
sodium chloride in an amount of from about 0.1 to about 0.5% by weight, based on the total weight of the effervescent composition; and
optionally, a processing aid.

37. The effervescent composition of claim 1, comprising:
isomalt in an amount of from about 20 to about 30% by weight, based on the total weight of the effervescent composition;
a glucose-polysaccharide blend in an amount of from about 30 to about 45% by weight, based on the total weight of the effervescent composition;
a sweetener in an amount of from about 0.1 to about 0.5% by weight, based on the total weight of the effervescent composition;
caffeine in an amount of from about 3 to about 5% by weight, based on the total weight of the effervescent composition;
taurine in an amount of from about 4 to about 6% by weight, based on the total weight of the effervescent composition;
vitamin C in an amount of from about 4 to about 6% by weight, based on the total weight of the effervescent composition;
sodium citrate in an amount of from about 1.5 to about 3.5% by weight, based on the total weight of the effervescent composition;
tartaric acid in an amount of from about 4 to about 6% by weight, based on the total weight of the effervescent composition;

citric acid in an amount of from about 4 to about 6% by weight, based on the total weight of the effervescent composition;
sodium bicarbonate in an amount of from about 8 to about 15% by weight, based on the total weight of the effervescent composition;
sodium chloride in an amount of from about 0.1 to about 0.5% by weight, based on the total weight of the effervescent composition; and
optionally, a processing aid.

38. The effervescent composition of claim 1, comprising:
isomalt in an amount of from about 22 to about 35% by weight, based on the total weight of the effervescent composition;
a glucose-polysaccharide blend in an amount of from about 28 to about 43% by weight, based on the total weight of the effervescent composition;
a sweetener in an amount of from about 0.1 to about 0.5% by weight, based on the total weight of the effervescent composition;
caffeine in an amount of from about 3 to about 5% by weight, based on the total weight of the effervescent composition;
L-theanine in an amount of from about 4 to about 6% by weight, based on the total weight of the effervescent composition;
*Panax ginseng* in an amount of from about 0.4 to about 0.6% by weight, based on the total weight of the effervescent composition;
sodium citrate in an amount of from about 0.5 to about 1.5% by weight, based on the total weight of the effervescent composition;
tartaric acid in an amount of from about 4 to about 6% by weight, based on the total weight of the effervescent composition;
citric acid in an amount of from about 4 to about 6% by weight, based on the total weight of the effervescent composition;
sodium bicarbonate in an amount of from about 8 to about 15% by weight, based on the total weight of the effervescent composition;
sodium chloride in an amount of from about 0.1 to about 0.5% by weight, based on the total weight of the effervescent composition;
optionally, citicoline or sunflower lecithin in an amount of from about 0.5 to about 1.5% by weight, based on the total weight of the effervescent composition; and
optionally, a processing aid.

\* \* \* \* \*